United States Patent
Schaefer et al.

(10) Patent No.: US 7,169,570 B2
(45) Date of Patent: Jan. 30, 2007

(54) METHOD TO IDENTIFY REGULATORS OF CELLULAR ACTIVATION USING BCL10

(75) Inventors: Brian C. Schaefer, Columbia, MD (US); Philippa Marrack, Denver, CO (US); John W. Kappler, Denver, CO (US)

(73) Assignee: National Jewish Medical and Research Center, Denver, CO (US)

( * ) Notice: Subject to any disclaimer, the term of this patent is extended or adjusted under 35 U.S.C. 154(b) by 190 days.

(21) Appl. No.: 10/795,157

(22) Filed: Mar. 4, 2004

(65) Prior Publication Data

US 2004/0265915 A1 Dec. 30, 2004

Related U.S. Application Data

(60) Provisional application No. 60/452,312, filed on Mar. 4, 2003.

(51) Int. Cl.
 C12Q 1/02 (2006.01)
 G01N 33/53 (2006.01)
 G01N 33/68 (2006.01)

(52) U.S. Cl. .................. 435/7.21; 435/7.24; 435/29; 435/377; 436/63; 436/86

(58) Field of Classification Search ............ 435/7.21, 435/7.24, 377; 436/63, 86
See application file for complete search history.

(56) References Cited

U.S. PATENT DOCUMENTS 5,976,819 A * 11/1999 Finkel et al. ............. 435/7.24
6,348,573 B1   2/2002 Nunez et al.
6,756,196 B2   6/2004 Bertin
2002/0081636 A1  6/2002 Bertin
2002/0086980 A1  7/2002 Bertin
2003/0113787 A1 * 6/2003 Bertin ....................... 435/6
2004/0072228 A1  4/2004 Glynne et al.
2004/0166099 A1  8/2004 Rao

FOREIGN PATENT DOCUMENTS

JP          08092285         9/1994

OTHER PUBLICATIONS

Egawa et al, Current Biology, vol. 13, 1252-1258, 2003.*
Schaefer et al, Proc. Natl. Acad. Sci. USA, vol. 101, 1004-1009, 2004.*
Bertin et al., *J Biol Chem.*, 276(15):11877-82 (2001).
Gaide et al., *FEBS Lett*, 496(203):121-7 (2001).
Gaide et al., *Nat Immunol*, 3(9):836-43 (2002).
Guiet and Vito, *J Cell Biol*, 148(6):1131-40 (2000).
Lucas et al., *J Biol Chem*, 276(22):19012-9 (2001).
McAllister Lucas et al., *J Biol Chem*, 276(3):30589-97 (2001).
Pomerantz et al., *EMBO J*, 21(19):5184-94 (2002).
Ruland et al., *Cell*, 104(1):33-42 (2001).
Wang et al., *Nat Immunol*, 3(9):830-5 (2002).

* cited by examiner

*Primary Examiner*—David Saunders
(74) *Attorney, Agent, or Firm*—Sheridan Ross, P.C.

(57) ABSTRACT

Disclosed are methods for evaluating the activation of Bcl10 in a cell in response to a putative stimulus, as well as methods for evaluating or identifying a regulatory compound which regulates activation of Bcl10-mediated signal transduction. These methods utilize the discovery of the activation-dependent formation in a cell of Bcl10 aggregates in a cell.

47 Claims, 9 Drawing Sheets
(6 of 9 Drawing Sheet(s) Filed in Color)

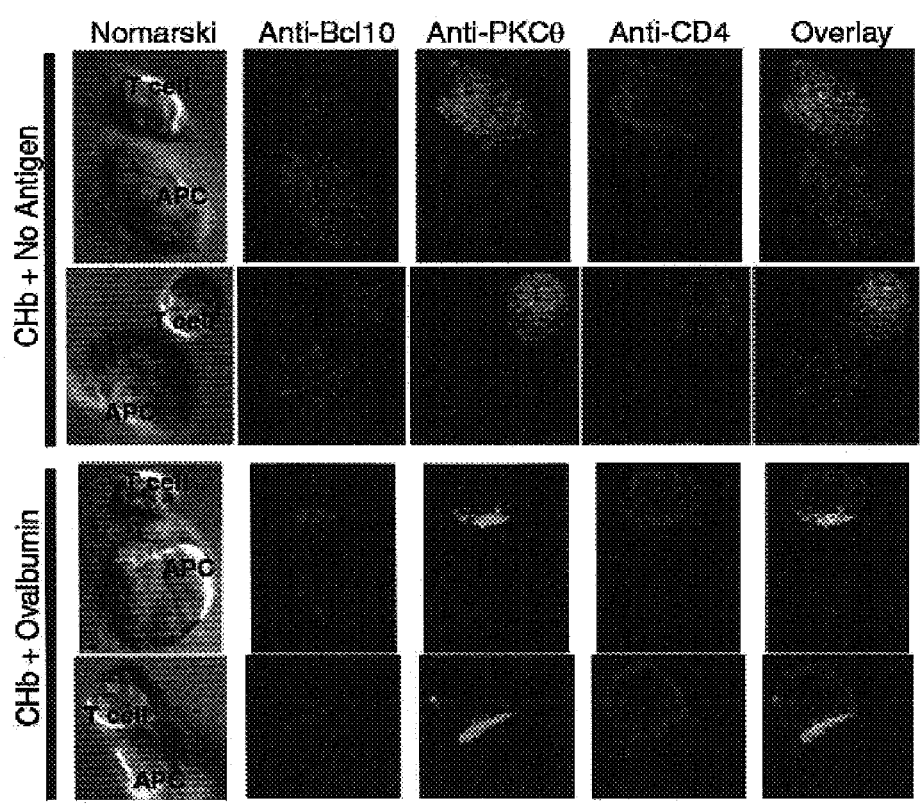

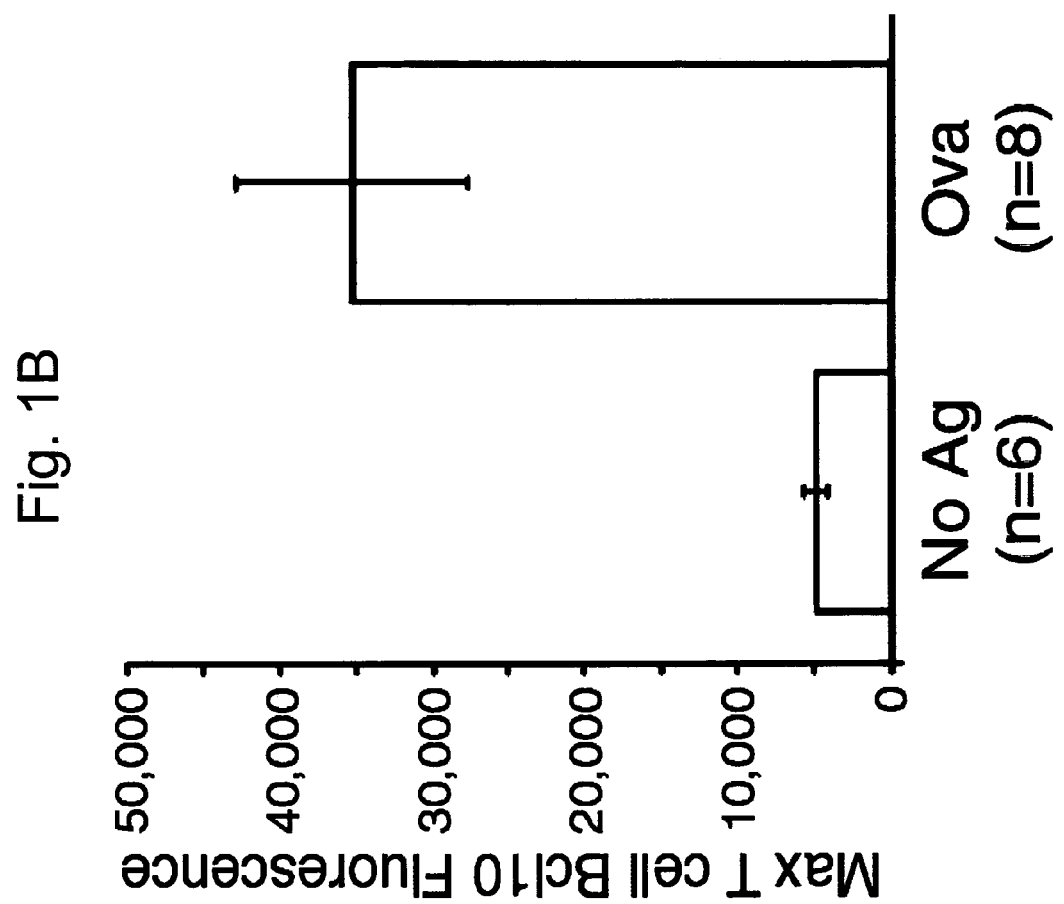

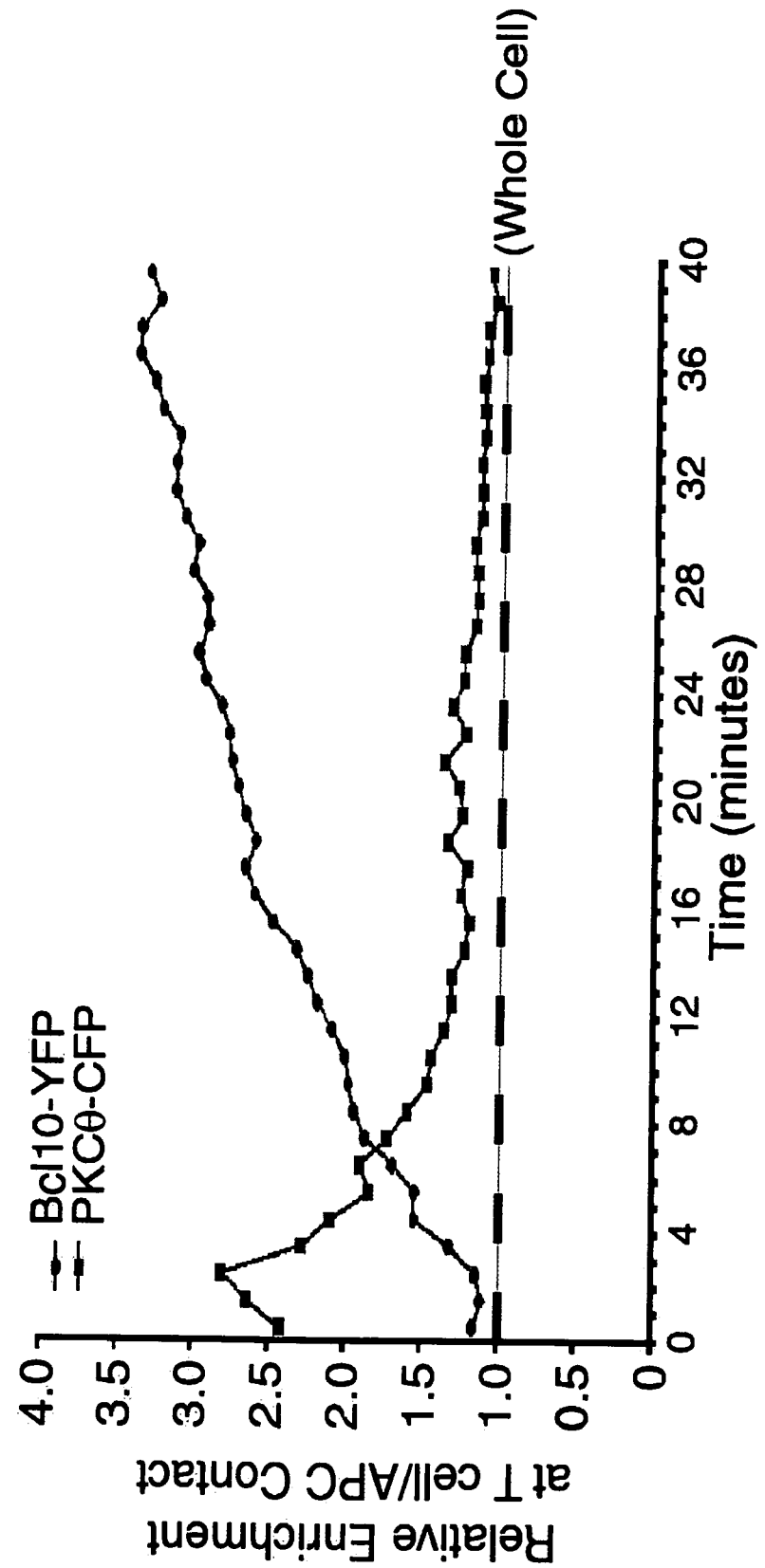

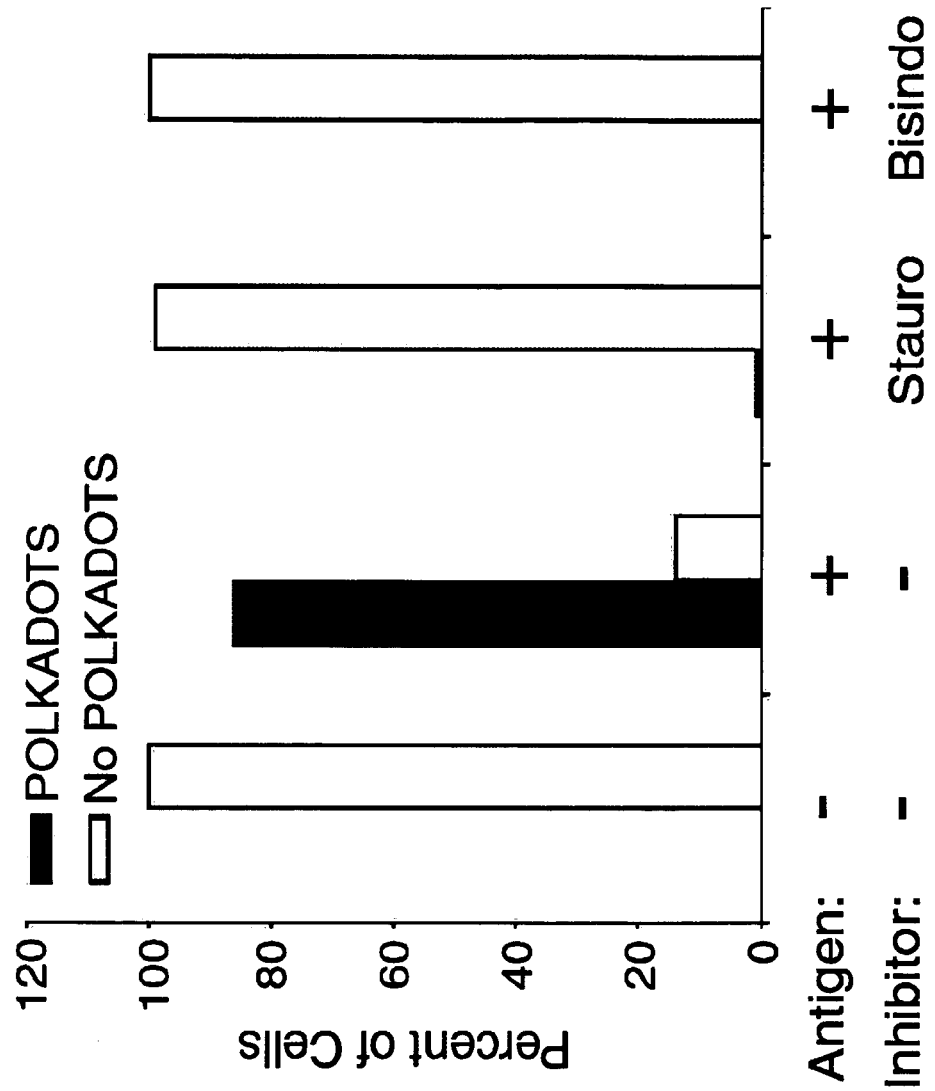

SEQUENCE LISTING

```
<160> NUMBER OF SEQ ID NOS: 7

<210> SEQ ID NO 1
<211> LENGTH: 2809
<212> TYPE: DNA
<213> ORGANISM: Homo sapiens
<220> FEATURE:
<221> NAME/KEY: CDS
<222> LOCATION: (706)..(1407)
<223> OTHER INFORMATION:

<400> SEQUENCE: 1
tttttttttt tttttgcttt cccgtttctt aaacattggc gttcccaagt ttctccttgg      60
tcctcctgtc attttatct actctcgtag cttcaaatac catctagttt atagtttatt     120
tagcatgttg tccaagccac cgtcttgggc ccagggctct acctgtagct tttcatccac    180
acttctcagg ttgcttctta cacagcgcca tagtagttaa aatacggtct ggggatagtc    240
gtctcttcat cagtctcccc cgacgacctg cgcaggcgtg gcttgaggaa acgcccgctg    300
tgggcggagc cacccgaaag gctccggtcg ggggcgggaa caggatcggc ccgcgggctg    360
gcgtcgatag gctgccgcag agacagggcg ggctctgcta agggacgcgc ctcgccgtgg    420
ggcggtgcct gcgcctgagc ctctacgaga gggaaggaac gctgctccga gctccgcgtc    480
gcgtcgcgta gattcgcgtc gccgtcgacc tcagaggcgg ggccggaagc gctacggttt    540 gaccccgag tccctctgtt cccgaagggg cggccgtctt tctcccgacc cgctccgcct    600
cctctccttc ttccccatta cccggaggcc gaagccccca gccagggcgg ggcggcgcag    660
cccgagctcc cggacccgga agaagcgcca tctcccgcct ccacc atg gag ccc acc    717
                                                  Met Glu Pro Thr
                                                    1 gca ccg tcc ctc acc gag gag gac ctc act gaa gtg aag aag gac gcc    765
Ala Pro Ser Leu Thr Glu Glu Asp Leu Thr Glu Val Lys Lys Asp Ala
  5              10                  15                  20 tta gaa aat tta cgt gta tac ctg tgt gag aaa atc ata gct gag aga    813
```

```
                                      -continued

Leu Glu Asn Leu Arg Val Tyr Leu Cys Glu Lys Ile Ile Ala Glu Arg
             25                  30                  35 cat ttt gat cat cta cgt gca aaa aaa ata ctc agt aga gaa gac act        861
His Phe Asp His Leu Arg Ala Lys Lys Ile Leu Ser Arg Glu Asp Thr
         40                  45                  50 gaa gaa att tct tgt cga aca tca agt aga aaa agg gct gga aaa ttg        909
Glu Glu Ile Ser Cys Arg Thr Ser Ser Arg Lys Arg Ala Gly Lys Leu
             55                  60                  65 tta gac tac tta cag gaa aac cca aaa ggt ctg gac acc ctt gtt gaa        957
Leu Asp Tyr Leu Gln Glu Asn Pro Lys Gly Leu Asp Thr Leu Val Glu
     70                  75                  80 tct att cgg cga gaa aaa aca cag aac ttc ctg ata cag aag att aca       1005
Ser Ile Arg Arg Glu Lys Thr Gln Asn Phe Leu Ile Gln Lys Ile Thr
 85                  90                  95                 100 gat gaa gtg ctg aaa ctt aga aat ata aaa cta gaa cat ctg aaa gga       1053
Asp Glu Val Leu Lys Leu Arg Asn Ile Lys Leu Glu His Leu Lys Gly
                105                 110                 115 cta aaa tgt agc agt tgt gaa cct ttt cca gat gga gcc acg aac aac       1101
Leu Lys Cys Ser Ser Cys Glu Pro Phe Pro Asp Gly Ala Thr Asn Asn
            120                 125                 130 ctc tcc aga tca aat tca gat gag agt aat ttc tct gaa aaa ctg agg       1149
Leu Ser Arg Ser Asn Ser Asp Glu Ser Asn Phe Ser Glu Lys Leu Arg
        135                 140                 145 gca tcc act gtc atg tac cat cca gaa gga gaa tcc agc acg acg ccc       1197
Ala Ser Thr Val Met Tyr His Pro Glu Gly Glu Ser Ser Thr Thr Pro
    150                 155                 160 ttt ttt tct act aat tct tct ctg aat ttg cct gtt cta gaa gta ggc       1245
Phe Phe Ser Thr Asn Ser Ser Leu Asn Leu Pro Val Leu Glu Val Gly
165                 170                 175                 180 aga act gaa aat acc atc ttc tct tca act aca ctt ccc aga cct ggg       1293
Arg Thr Glu Asn Thr Ile Phe Ser Ser Thr Thr Leu Pro Arg Pro Gly
                185                 190                 195 gac cca ggg gct cct cct ttg cca cca gat cta cag tta gaa gaa gaa       1341
Asp Pro Gly Ala Pro Pro Leu Pro Pro Asp Leu Gln Leu Glu Glu Glu
            200                 205                 210 gga act tgt gca aac tct agt gag atg ttt ctt ccc tta aga tca cgt       1389
Gly Thr Cys Ala Asn Ser Ser Glu Met Phe Leu Pro Leu Arg Ser Arg
        215                 220                 225 act gtt tca cga caa tga cactttattg cctttaatt tttaatgatg              1437
Thr Val Ser Arg Gln
    230 acaaaaatg ttttaaagaa tatgactttt tataaaatgg ctgtaatcat ttgtttacat     1497
ttgatgcatg tcttttaaaa tgcaatgtaa gcatactttg taaataggat ttttagaatt     1557
aaaaaagcat acttctagga tagctaactg taaatcatgt tgatcatgta ctttttagta    1617
atttcttttt ttccttttta aggtctttca gtactttttt aaatattttc tattttaaga    1677
ctgattttaa tagggaatat atctctattt gagaatagac ccttactagg aagaacgttt    1737
tttcctcagt gcatttgtgc tagaaatttt caagagtcta atagtctttg ccagtcattc    1797
agcagcaaat tttcagcatt aagctgttcc tgttcagtaa taaaaccggt cactgatggg    1857
aaaactgcca atatagaaaa ataaaaatct cttttccact ccattgtcgt ataggcatgt    1917
aaacagcctc ttttttgatac tggaggaaca cttgatggag tgtgagccac ctaagatctc   1977
ggtttgccaa aattcatttc taattaacct tactaattat actactttgt taggattttc    2037
acattcttgg cttaatcatt ttcattccta agaaaaata tcttggccta aacctcagtt     2097
attacatgta atttgatgag gtatttttc cttttttctt tttttttttt ttgagacagt     2157
```

-continued

```
cttgctctat cgcccaggct ggagtgcagt ggcgcattct aggctcactg caacttctgc   2217
ctcccatgct tacgtgatcc tctcacctca gcctctcaag taatatagct gagactacaa   2277
gtgtgtgcca ccatgcctca ctaatttttg tattattttt gtagagacgg tgttttgcca   2337
tgttggccag gctggtcttg aactcctgga ctcaagcaac ctacccagcg tggcctccca   2397
aagtgctggg attacagaca cgagccacct cacctagcct gatgagattt ttaaaaaata   2457
ttttctctgt acttttcatt ctcttttaat gaggaccaat gtacagttga aataactgga   2517
acaaattatt tttggtgtgt gtgacaattc tgtttttaat gctatttgaa caagtgggcc   2577
attagccaga tttgtctttt tgttgtaaaa caaaatttga ctaattttac atgtttataa   2637
atcttatgct ctcactgttt gtttttattt aaattacaat tttatctgtt tcctgacatt   2697
gtctcctata tatttctatt attaattgca aaaacataga aatggaaatt ttgctatcaa   2757
caataaaatt tttttaaagt aaaaaaaaaa aaaaaaaaaa aaaaaaaaaa aa           2809
```

<210> SEQ ID NO 2
<211> LENGTH: 233
<212> TYPE: PRT
<213> ORGANISM: Homo sapiens

<400> SEQUENCE: 2

```
Met Glu Pro Thr Ala Pro Ser Leu Thr Glu Glu Asp Leu Thr Glu Val
1               5                   10                  15

Lys Lys Asp Ala Leu Glu Asn Leu Arg Val Tyr Leu Cys Glu Lys Ile
            20                  25                  30

Ile Ala Glu Arg His Phe Asp His Leu Arg Ala Lys Lys Ile Leu Ser
        35                  40                  45

Arg Glu Asp Thr Glu Glu Ile Ser Cys Arg Thr Ser Ser Arg Lys Arg
    50                  55                  60

Ala Gly Lys Leu Leu Asp Tyr Leu Gln Glu Asn Pro Lys Gly Leu Asp
65                  70                  75                  80

Thr Leu Val Glu Ser Ile Arg Arg Glu Lys Thr Gln Asn Phe Leu Ile
                85                  90                  95

Gln Lys Ile Thr Asp Glu Val Leu Lys Leu Arg Asn Ile Lys Leu Glu
            100                 105                 110

His Leu Lys Gly Leu Lys Cys Ser Ser Cys Glu Pro Phe Pro Asp Gly
        115                 120                 125

Ala Thr Asn Asn Leu Ser Arg Ser Asn Ser Asp Glu Ser Asn Phe Ser
    130                 135                 140

Glu Lys Leu Arg Ala Ser Thr Val Met Tyr His Pro Glu Gly Glu Ser
145                 150                 155                 160

Ser Thr Thr Pro Phe Phe Ser Thr Asn Ser Ser Leu Asn Leu Pro Val
                165                 170                 175

Leu Glu Val Gly Arg Thr Glu Asn Thr Ile Phe Ser Ser Thr Thr Leu
            180                 185                 190

Pro Arg Pro Gly Asp Pro Gly Ala Pro Pro Leu Pro Pro Asp Leu Gln
        195                 200                 205

Leu Glu Glu Glu Gly Thr Cys Ala Asn Ser Ser Glu Met Phe Leu Pro
    210                 215                 220

Leu Arg Ser Arg Thr Val Ser Arg Gln
225                 230
```

<210> SEQ ID NO 3
<211> LENGTH: 1760
<212> TYPE: DNA

```
<213> ORGANISM: Mus musculus
<220> FEATURE:
<221> NAME/KEY: CDS
<222> LOCATION: (82)..(783)
<223> OTHER INFORMATION:

<400> SEQUENCE: 3
```

| | | |
|---|---|---|
| cacagcctga ttcccggagg cccgagccct tagtctgggc ggggtggcgc gggccggaag | | 60 |
| gacgccatcc cggcctgggc c atg gag gct ccc gca ccg tcc ctc acg gag<br>                                    Met Glu Ala Pro Ala Pro Ser Leu Thr Glu<br>                                    1              5                   10 | | 111 |
| gag gat ttg act gaa gtg aag aag gac gct tta gag aat tta cgt gtt<br>Glu Asp Leu Thr Glu Val Lys Lys Asp Ala Leu Glu Asn Leu Arg Val<br>              15                     20                     25 | | 159 |
| tac ctg tgt gag aaa atc ata gct gag aga cat ttt gat cat cta cgt<br>Tyr Leu Cys Glu Lys Ile Ile Ala Glu Arg His Phe Asp His Leu Arg<br>        30                     35                     40 | | 207 |
| gca aaa aaa ata cta agt aga gaa gac aca gaa gaa att tct tgc cga<br>Ala Lys Lys Ile Leu Ser Arg Glu Asp Thr Glu Glu Ile Ser Cys Arg<br>       45                     50                     55 | | 255 |
| act tca agt aga aaa cgg gct ggg aag ttg tta gac tac tta cag gag<br>Thr Ser Ser Arg Lys Arg Ala Gly Lys Leu Leu Asp Tyr Leu Gln Glu<br>   60                     65                     70 | | 303 |
| aac ccc agg ggc ctg gac acc ctg gtg gaa tcc atc cgc agg gag aaa<br>Asn Pro Arg Gly Leu Asp Thr Leu Val Glu Ser Ile Arg Arg Glu Lys<br>75                     80                     85                     90 | | 351 |
| aca cag agc ttc ctg att cag aag ata acg gat gag gtg cta aag ctt<br>Thr Gln Ser Phe Leu Ile Gln Lys Ile Thr Asp Glu Val Leu Lys Leu<br>              95                     100                   105 | | 399 |
| cgg aat ata aaa ctg gag cac ctc aaa ggc ctg aag tgc agc agc tgt<br>Arg Asn Ile Lys Leu Glu His Leu Lys Gly Leu Lys Cys Ser Ser Cys<br>          110                     115                   120 | | 447 |
| gag ccc ttt gca gcc gga gcc acc aac aac ctc tct agg tgc aat tcc<br>Glu Pro Phe Ala Ala Gly Ala Thr Asn Asn Leu Ser Arg Cys Asn Ser<br>       125                     130                     135 | | 495 |
| gat gag agc aat ctc tct gag aaa cag aga gca tcc act gtc atg tac<br>Asp Glu Ser Asn Leu Ser Glu Lys Gln Arg Ala Ser Thr Val Met Tyr<br>140                     145                     150 | | 543 |
| cac ccg gag gga gag tcc agc acg gct ccc ttc ttc tct atg gcg tcg<br>His Pro Glu Gly Glu Ser Ser Thr Ala Pro Phe Phe Ser Met Ala Ser<br>155                     160                     165                   170 | | 591 |
| tcc ctg aac ttg cca gtc ctg gaa gtt ggc agg act gaa aac agc agc<br>Ser Leu Asn Leu Pro Val Leu Glu Val Gly Arg Thr Glu Asn Ser Ser<br>              175                     180                     185 | | 639 |
| ttc tct tca gcc act ctt cct cga cct ggg gac cct ggg gct ccc cct<br>Phe Ser Ser Ala Thr Leu Pro Arg Pro Gly Asp Pro Gly Ala Pro Pro<br>          190                     195                   200 | | 687 |
| ttg ccc cca gac ctt cgg ttg gaa gag ggg gga agt tgt gga aac tca<br>Leu Pro Pro Asp Leu Arg Leu Glu Glu Gly Gly Ser Cys Gly Asn Ser<br>       205                     210                     215 | | 735 |
| agt gag atg ttt ctc ccc tta cgg tca cgg gct ctt tca cgc caa tga<br>Ser Glu Met Phe Leu Pro Leu Arg Ser Arg Ala Leu Ser Arg Gln<br>220                     225                     230 | | 783 |
| tacatcaccg cctagttgtt ttactagtga tgcaaaatgc tgtgaaggag gccatctttc | | 843 |
| tatacaaacc acggtgacag gtcactcaca ttcgatgcgt gcctttaaaa tcagtgtaca | | 903 |
| cattctctgt aaataggatt tgttagggta agaagcgct ctgggcggc gtggtgtaaa | | 963 |
| tcatggtggt cgtgactttt ccataatgtc ctttcttttt tattattttt aggtgtttgc | | 1023 |
| gtattttgaa cttttcataa gattaatttt atcggaatat ttctcaattt gagaaaacaa | | 1083 |

-continued

```
cttgtggatt gggaataatg tttttagcac atttatgcta caaatttca gtctgattgt    1143 tttcccact gatctggcag tatattttag cagtaagctg ttgtgtttca ggaaagctgg     1203
acacgggaaa gctgccgaca cactcagcag tgtcccactc cttagttctg agaagccgtc   1263
gggttctgag gagacacctg gtggcactga gcctggtgac ctcagtgggc caaaatttgt    1323
tttatactca ccctgccagc gtgagtgtct tactttcaca ggccttgtgt cctcagtctt    1383
atcttaaagg atgttatctt ggcagggcat cacttgtaat taatggatga tacttgtaat   1443
tgactaaagt cctcgctctg agccgtttgt tctggctccg agagcgctga catgtgaagc   1503
atggtgagca gcgagggaac tgacaggatg tggccgtggc cagtgtggct ttagtgtttg   1563
catcaggcag ccaccagctc catccgtgtt cttactgctt tacaaagttt gactaacttt   1623
acacatttta aaaatgctga ttgtcttcgt ttaaattata attttaccta tttcttgaca    1683
tctaactcct attcatttct attatttaaa aattaagaaa tgaaaatttg ctattaacaa   1743
taaagttttt ttaatgt                                                   1760
```

<210> SEQ ID NO 4
<211> LENGTH: 233
<212> TYPE: PRT
<213> ORGANISM: Mus musculus

<400> SEQUENCE: 4

```
Met Glu Ala Pro Ala Pro Ser Leu Thr Glu Glu Asp Leu Thr Glu Val
 1               5                  10                  15

Lys Lys Asp Ala Leu Glu Asn Leu Arg Val Tyr Leu Cys Glu Lys Ile
            20                  25                  30

Ile Ala Glu Arg His Phe Asp His Leu Arg Ala Lys Lys Ile Leu Ser
        35                  40                  45

Arg Glu Asp Thr Glu Glu Ile Ser Cys Arg Thr Ser Ser Arg Lys Arg
    50                  55                  60

Ala Gly Lys Leu Leu Asp Tyr Leu Gln Glu Asn Pro Arg Gly Leu Asp
65                  70                  75                  80

Thr Leu Val Glu Ser Ile Arg Arg Glu Lys Thr Gln Ser Phe Leu Ile
                85                  90                  95

Gln Lys Ile Thr Asp Glu Val Leu Lys Leu Arg Asn Ile Lys Leu Glu
            100                 105                 110

His Leu Lys Gly Leu Lys Cys Ser Ser Cys Glu Pro Phe Ala Ala Gly
        115                 120                 125

Ala Thr Asn Asn Leu Ser Arg Cys Asn Ser Asp Glu Ser Asn Leu Ser
    130                 135                 140

Glu Lys Gln Arg Ala Ser Thr Val Met Tyr His Pro Glu Gly Glu Ser
145                 150                 155                 160

Ser Thr Ala Pro Phe Phe Ser Met Ala Ser Ser Leu Asn Leu Pro Val
                165                 170                 175

Leu Glu Val Gly Arg Thr Glu Asn Ser Ser Phe Ser Ser Ala Thr Leu
            180                 185                 190

Pro Arg Pro Gly Asp Pro Gly Ala Pro Pro Leu Pro Pro Asp Leu Arg
        195                 200                 205

Leu Glu Glu Gly Gly Ser Cys Gly Asn Ser Ser Glu Met Phe Leu Pro
    210                 215                 220

Leu Arg Ser Arg Ala Leu Ser Arg Gln
225                 230
```

-continued

```
<210> SEQ ID NO 5
<211> LENGTH: 1668
<212> TYPE: DNA
<213> ORGANISM: Rattus norvegicus
<220> FEATURE:
<221> NAME/KEY: CDS
<222> LOCATION: (126)..(827)
<223> OTHER INFORMATION:

<400> SEQUENCE: 5
gtgaaccggc ggttcccccg cttctgttcc tagtcctccc aagtcacagc ccgattcccg      60
gaggcccgag cccttagcca gggcggggtg gcgcgggccg aaaggacgcc atcccggcct     120 cggcc atg gag gct ccc gcg ccg tct ctc acg gag gag gac tta act gaa    170
      Met Glu Ala Pro Ala Pro Ser Leu Thr Glu Glu Asp Leu Thr Glu
      1               5                  10                  15 gtg aag aag gac gct tta gag aat ttg cga gtt tac ctg tgt gag aaa      218
Val Lys Lys Asp Ala Leu Glu Asn Leu Arg Val Tyr Leu Cys Glu Lys
            20                  25                  30 atc ata gct gag aga cat ttt gat cat cta cga gca aaa aaa att cta      266
Ile Ile Ala Glu Arg His Phe Asp His Leu Arg Ala Lys Lys Ile Leu
        35                  40                  45 agt aga gaa gac aca gaa gaa att tct tgc cga act tca agt aga aaa      314
Ser Arg Glu Asp Thr Glu Glu Ile Ser Cys Arg Thr Ser Ser Arg Lys
    50                  55                  60 agg gct ggg aag ttg tta gac tac tta cag gaa aac ccc aag gga ctg      362
Arg Ala Gly Lys Leu Leu Asp Tyr Leu Gln Glu Asn Pro Lys Gly Leu
65                  70                  75 gac acc ctt gtg gaa tcc att cgc agg gag aaa aca cag aac ttc ctg      410
Asp Thr Leu Val Glu Ser Ile Arg Arg Glu Lys Thr Gln Asn Phe Leu
80                  85                  90                  95 att cag aag ata acg gat gag gtg cta aag ctt cgg aat ata aaa ctg      458
Ile Gln Lys Ile Thr Asp Glu Val Leu Lys Leu Arg Asn Ile Lys Leu
                100                 105                 110 gag cac ctc aaa ggc ctg aag tgc agt agc tgt gag ccc ttc gca gct      506
Glu His Leu Lys Gly Leu Lys Cys Ser Ser Cys Glu Pro Phe Ala Ala
            115                 120                 125 gga gcc acc aac aac ctt tct agg tcc aat tct gat gag agc aac ttc      554
Gly Ala Thr Asn Asn Leu Ser Arg Ser Asn Ser Asp Glu Ser Asn Phe
        130                 135                 140 tcc gag aaa cag aga cca tcc acg gtc atc tac cat cca gag gga gag      602
Ser Glu Lys Gln Arg Pro Ser Thr Val Ile Tyr His Pro Glu Gly Glu
    145                 150                 155 tcg agc act gct ccc ttc ttc tct acc gag tca tcc ctg aat ctg ccg      650
Ser Ser Thr Ala Pro Phe Phe Ser Thr Glu Ser Ser Leu Asn Leu Pro
160                 165                 170                 175 gtc ctg gaa gtt ggc agg ctg gaa aac agc agc ttc tct tca gcc tcg      698
Val Leu Glu Val Gly Arg Leu Glu Asn Ser Ser Phe Ser Ser Ala Ser
                180                 185                 190 ctt cct cgg cct ggg gac cct ggg gcc ccc cct ttg ccc cca gac ctg      746
Leu Pro Arg Pro Gly Asp Pro Gly Ala Pro Pro Leu Pro Pro Asp Leu
            195                 200                 205 cgg tta gaa gag ggg ggg agt tgt gga aac tca agt gag atg ttt ctc      794
Arg Leu Glu Glu Gly Gly Ser Cys Gly Asn Ser Ser Glu Met Phe Leu
        210                 215                 220 ccc tta cgg tca cgg gct ctt tca cgg cag tga caggtcactg cgagttgttc     847
Pro Leu Arg Ser Arg Ala Leu Ser Arg Gln
    225                 230 taatagtggt gcaaatggtg tggtggatat catcttttta taaatcacgg gatgcgcgtc     907
ttaaatcaca ggtgcacata acattctctg taaataggat tggaagtgta atggagcaca     967 ctctagggc agcttggtgt aaatcatggt ggtcgtgtac ttttcagcat tgtccttttt    1027
```

```
tattatttta agtgttttgg tattttgaac ttttttataa gactaatttt atcaaaatat   1087
ttctcaattt gagaaaacaa cttgtggacc gaaaacccta caagttttcc gcctggttgt   1147
gtttcctggt gatctgacag tacattttag cagtaagctg ttctgacttt caggaaagcc   1207
agacatgggg agagctgctg acacaccctc aggagaatgt cccactccgt gcttctgaga   1267
agccgtcagg ttctgaggaa acacctgatg gcgttgagcc ttgtgatctc agttggccag   1327
aatttgttgt ataccttgcc agtatgattg tctttgcctt ttacagacct tgtgtcctca   1387
gtcttggcct gaagaatgtt atcccggcag ggcgctcctt gtaattaatt ggtaacactt   1447
gtaattagct aaagtccttg ctctgagcct ttccttctct gccgatgagc actgccatgt   1507
ggagttactg tattacaaag ttggctaact ttacacattt aaaaagtgct gattattttc   1567
ttttaaatta tacctatttc tgacatctaa ctcctatata tttctattat ttaaaaatta   1627
agaaatgaaa gtttctatt aacaataaaa ttttttttaag t   1668
```

<210> SEQ ID NO 6
<211> LENGTH: 233
<212> TYPE: PRT
<213> ORGANISM: Rattus norvegicus

<400> SEQUENCE: 6

```
Met Glu Ala Pro Ala Pro Ser Leu Thr Glu Glu Asp Leu Thr Glu Val
1               5                   10                  15

Lys Lys Asp Ala Leu Glu Asn Leu Arg Val Tyr Leu Cys Glu Lys Ile
                20                  25                  30

Ile Ala Glu Arg His Phe Asp His Leu Arg Ala Lys Lys Ile Leu Ser
            35                  40                  45

Arg Glu Asp Thr Glu Glu Ile Ser Cys Arg Thr Ser Ser Arg Lys Arg
        50                  55                  60

Ala Gly Lys Leu Leu Asp Tyr Leu Gln Glu Asn Pro Lys Gly Leu Asp
65                  70                  75                  80

Thr Leu Val Glu Ser Ile Arg Arg Glu Lys Thr Gln Asn Phe Leu Ile
                85                  90                  95

Gln Lys Ile Thr Asp Glu Val Leu Lys Leu Arg Asn Ile Lys Leu Glu
                100                 105                 110

His Leu Lys Gly Leu Lys Cys Ser Ser Cys Glu Pro Phe Ala Ala Gly
            115                 120                 125

Ala Thr Asn Asn Leu Ser Arg Ser Asn Ser Asp Glu Ser Asn Phe Ser
        130                 135                 140

Glu Lys Gln Arg Pro Ser Thr Val Ile Tyr His Pro Glu Gly Glu Ser
145                 150                 155                 160

Ser Thr Ala Pro Phe Phe Ser Thr Glu Ser Ser Leu Asn Leu Pro Val
                165                 170                 175

Leu Glu Val Gly Arg Leu Glu Asn Ser Ser Phe Ser Ser Ala Ser Leu
            180                 185                 190

Pro Arg Pro Gly Asp Pro Gly Ala Pro Pro Leu Pro Pro Asp Leu Arg
        195                 200                 205

Leu Glu Glu Gly Gly Ser Cys Gly Asn Ser Ser Glu Met Phe Leu Pro
210                 215                 220

Leu Arg Ser Arg Ala Leu Ser Arg Gln
225                 230
```

<210> SEQ ID NO 7
<211> LENGTH: 7

```
<212> TYPE: PRT
<213> ORGANISM: Artificial sequence
<220> FEATURE:
<223> OTHER INFORMATION: synthetic peptide

<400> SEQUENCE: 7

Gly Arg Val Glu Leu Gly Arg
1               5
```

METHOD TO IDENTIFY REGULATORS OF CELLULAR ACTIVATION USING BCL10

CROSS-REFERENCE TO RELATED APPLICATIONS

This application claims the benefit of priority under 35 U.S.C. § 119(e) from U.S. Provisional Application Ser. No. 60/452,312, filed Mar. 4, 2003, entitled "Method to Identify Regulators of Cellular Activation Using Bcl10". The entire disclosure of U.S. Provisional Application Ser. No. 60/452,312 is incorporated herein by reference.

GOVERNMENT SUPPORT

This invention was supported in part with funding provided by NIH Grant Nos. AI-17134, AI-18785, AI-52225, AI-22295 and AI-23764, each awarded by the National Institutes of Health, and by Grant No. CO73JN, awarded by the Uniformed Services University of the Health Sciences. The government may have certain rights to this invention.

FIELD OF THE INVENTION

The present invention generally relates to methods for the assessment of cellular activation in cells that express Bcl10, using Bcl10-dependent activation characteristics as a marker. Specifically, the invention relates to the use of the formation of aggregated Bcl10 polymers as an indicator of cell activation and to identify compounds that regulate cell activation.

BACKGROUND OF THE INVENTION

T cell receptor (TCR)-regulated activation of the transcription factor NF-κB is of paramount importance in the T cell response to antigen. Because T cells cannot enter S-phase when TCR-modulated NF-κB activation is blocked (1), the ability of T cells to divide and acquire effector functions is crucially dependent upon delivery of this signal. Recent data from gene-targeted mice have demonstrated that the serine-threonine kinase, PKCθ, the caspase recruitment domain (CARD) proteins, Bcl10 and CARMA1, and the "paracaspase" MALT1, are intermediates in TCR activation of NF-κB (2–8).

A subset of T cell transmembrane and cytoplasmic molecules segregate into discrete zones of enrichment, following interaction with stimulatory antigen presenting cells (APCs) (9, 10). These regions, called supramolecular activation clusters (SMACs) form a bull's-eye pattern at the interface between the T cell and the APC, which has been termed the immunological synapse (11, 12). The T cell receptor is concentrated in the central zone of the SMAC, called the c-SMAC. PKCθ is also enriched in this zone, associated indirectly with the cytoplasmic face of the TCR. The adhesion molecule LFA-1 is enriched in a peripheral zone called the p-SMAC, which surrounds the c-SMAC (9). The cytoskeletal organizing protein talin is also enriched in the p-SMAC (9), and may be directly associated with the cytoplasmic tail of LFA-1 (13).

Thus, gene inactivation studies have established that PKCθ is required for TCR activation of NF-κB, and microscopy analyses have shown that PKCθ translocates to the c-SMAC in response to antigen stimulation.

The B cell antigen receptor (BCR) complex is composed of membrane immunoglobulin (mIg) noncovalently associated with heterodimers of Ig-α and Ig-β. These signal transducing subunits contain a conserved ITAM motif (immunoreceptor tyrosine-based activation motif) required for signal transduction (39). Aggregation of the BCR by multivalent antigen initiates transphosphorylation of the Ig-α and Ig-β ITAM motifs and activation of receptor-associated kinases (for review see 40,41,42). Phosphorylated ITAMs recruit additional effectors such as PI3-K, PLC-γ and members of the Ras/MAPK pathway. The BCR signal transduction pathway induces the activation of various transcription factors, including NF-κB. These signaling events are responsible for B cell proliferation, and increased expression of activation markers such as MHC class II and CD86, that are required to prime the B cell for subsequent interactions with $T_h$ cells.

B-cell CLL/lymphoma 10 (Bcl10) is encoded by a gene (bcl10) that is involved in the chromosomal translocation t(1;14)(p22;q32) found in mucosa-associated lymphoid tissue lymphoma (MALT lymphoma). Bcl10 is an intracellular protein that is also essential for nuclear factor (NF)-κB activation after lymphocyte antigen receptor stimulation. The importance of the Bcl10 signaling pathway in lymphocyte activation (B and T lymphocytes) has recently been illustrated by the bcl10 knockout mouse. Although inactivation of both copies of Bcl10 results in embryo lethality in about 30% of day 18.5 embryos, the remaining 70% of mice are viable and superficially normal. However, these mice do have one prominent defect—both B cells and T cells are nearly completely non-responsive to stimulation through their antigen receptors (e.g., the cells do not divide and do not mount effective responses to antigen/pathogens). This non-responsiveness was shown to be the result of failure to activate the NF-κB transcription factor. Importantly, other signaling pathways that regulate NF-κB (lipopolysaccharide (LPS), tumor necrosis factor (TNF), interleukin-1 (IL-1)) in these same bcl10 knockout T and B lymphocytes remain intact. Thus, loss of Bcl10 signaling apparently results in a very specific block of antigen receptor-mediated activation of NF-κB in lymphocytes.

Therefore, a drug that blocks activation of either Bcl10 or a signaling molecule that acts upstream of Bcl10 in lymphocytes is expected to specifically inhibit the responses of lymphocytes to antigen receptor stimulation. Because autoimmune diseases and graft rejection are dependent upon antigen receptor stimulation of lymphocytes, drugs that inhibit Bcl10 signaling should be useful as treatments for these conditions. Also, MALT lymphomas involve the dis-regulated expression of Bcl10, and thus, drugs that directly inhibit Bcl10 signaling should be useful as chemotherapeutic agents in the treatment of these lymphomas. Finally, since Bcl10 is ubiquitously expressed, drugs that inhibit Bcl10-dependent activation are expected to have other applications.

The identification of novel drugs that target specific signaling pathways is nearly impossible without a specific, high-throughput screening assay. In fact, now that large drug companies have access to libraries containing millions of small molecule compounds (potential drugs), the lack of good quality, high-throughput screening assays represents the major bottleneck in the identification of novel drugs. Therefore, there is a need in the art for improved, high-throughput drug screening assays, and particularly for those that may provide therapeutic compounds for treating a wide variety of immunologically-mediated and immunologically-benefitted disorders.

SUMMARY OF THE INVENTION

One embodiment of the present invention relates to a method for evaluating activation of Bcl10 in a cell in response to a putative stimulus. The method includes the steps of: (a) contacting an isolated cell having a Bcl10 signal transduction pathway with a putative stimulus; and (b) detecting whether Bcl10 expressed by the cell polymerizes into aggregates in the cell after contact with the putative stimulus as compared to in the absence of the putative stimulus. The polymerization of Bcl10 into aggregates in the cell indicates Bcl10-mediated activation of the cell.

The step of detecting can be performed by any suitable detection method, including, but not limited to, using microscopy to visualize Bcl10 in the cell (e.g., using fluorescent microscopy to visualize Bcl10 in the cell); using an antibody that selectively binds to Bcl10; detecting a recombinant Bcl10 protein expressed by the cell; detecting a Bcl10-reporter fusion protein expressed by the cell; using biochemical extraction of Bcl10 from cells and detection of Bcl10 aggregates by biochemical fractionation techniques (e.g., gel electrophoresis and gradient centrifugation); measuring changes in a refractive index of intact cells or biochemical extracts of cells; and measuring changes in the light scatter properties of cells.

In one embodiment, the method further includes a step of detecting translocation of the aggregates of Bcl10 to a site of contact between the cell and the putative stimulus, the translocation being further indicative of Bcl10-mediated activation of the cell. In another embodiment, the method further includes a step of detecting whether there is change in the level of Bcl10 expression in the cell in the presence of the putative stimulus as compared to the level of Bcl10 expression in the absence of the putative stimulus, a change in Bcl10 expression being further indicative Bcl10-mediated activation of the cell. In another embodiment, the method further includes a step of detecting whether Bcl10 is phosphorylated in the cell, the phosphorylation of Bcl10 being further indicative of Bcl10-mediated activation of the cell.

In one embodiment, the cell is a lymphocyte expressing an antigen receptor, and the polymerization of Bcl10 into aggregates in the cell in the presence of the putative stimulus indicates activation of the cell through an antigen receptor-associated, Bcl10 signal transduction pathway.

For example, in one aspect of the invention, the cell is a T lymphocyte, which can include, but is not limited to, a primary lymph node T lymphocyte, a primary splenic T lymphocyte, a T lymphocyte from a transgenic mouse, a T lymphocyte clone or a T lymphocyte hybridoma. In this aspect of the invention, the method can include the following steps: (a) culturing a T lymphocyte expressing a T cell receptor (TCR) with a putative stimulus for activating the T lymphocyte through the TCR signal transduction pathway; and (b) detecting whether Bcl10 expressed by the T lymphocyte polymerizes into aggregates in the T lymphocyte in the presence of the putative stimulus as compared to in the absence of the putative stimulus, wherein the polymerization of Bcl10 into aggregates in the T lymphocyte indicates Bcl10-mediated activation of the T lymphocyte.

In this aspect of the invention, the putative stimulus can include, but is not limited to, an antigen presenting cell expressing a major histocompatibility complex (MHC)-antigen complex wherein the antigen is bound to an antigen binding site of the MHC; an antibody that selectively binds to and activates the TCR; an antibody that selectively binds to and activates CD3; a purified, soluble MHC-peptide complex; a T lymphocyte mitogen (e.g., PHA, conconavalin A, a phorbol ester); an activator of protein kinase C (PKC); and a T lymphocyte superantigen. In one aspect, the step of culturing comprises culturing the T lymphocyte with an antigen presenting cell expressing an MHC-antigen complex, wherein the antigen is bound to an antigen binding site of the MHC, wherein, if the TCR binds to the MHC-antigen complex, an antigen-specific site of contact between the T lymphocyte and the antigen presenting cell is formed.

In another aspect of this embodiment of the invention, the lymphocyte is a B lymphocyte, which can include, but is not limited to, a primary B lymphocyte, a B lymphocyte from a transgenic mouse, or a B lymphocyte hybridoma. In this aspect of the invention, the method can include the steps of: (a) culturing a B lymphocyte expressing a B cell antigen receptor (BCR) with a putative stimulus for activating the B lymphocyte through the BCR; and (b) detecting whether Bcl10 expressed by the B lymphocyte polymerizes into aggregates in the B lymphocyte in the presence of the putative stimulus as compared to in the absence of the putative stimulus, wherein the polymerization of Bcl10 into aggregates in the B lymphocyte indicates Bcl10-mediated activation of the lymphocyte.

In this aspect of the invention, the putative stimulus can include, but is not limited to, an antibody that selectively binds to and activates the BCR; an activator of protein kinase C (PKC); a phorbol ester; antibodies that selectively bind to and activate transmembrane forms of IgM, IgD, IgG, IgA or IgE; antibodies that selectively bind to and activate the immunoglobulin-associated signaling molecules Ig-$\alpha$ or Ig-$\beta$; and polyvalent ligands for IgM, IgD, IgG, IgA or IgE (e.g., polyvalent cognant antigen, lectins that bind immunoglobulin, and compounds that aggregate surface immunoglobulin).

Yet another embodiment of the present invention relates to a method to identify a regulatory compound which regulates activation of Bcl10-mediated signal transduction. The method includes the steps of: (a) contacting an isolated cell having a Bcl10 signal transduction pathway with a putative regulatory compound and a stimulus, under conditions in which, in the absence of the putative regulatory compound, the stimulus activates the Bcl10 signal transduction pathway such that Bcl10 expressed by the cell polymerizes into aggregates in the cell; and (b) detecting whether the putative regulatory compound increases or decreases the level of the aggregates of Bcl10 in the cell in as compared to in the absence of the putative regulatory compound, wherein an increase or decrease in the level of the aggregates of Bcl10 in the presence of the putative regulatory compound indicates that the compound regulates Bcl10-mediated signal transduction in the cell. A decrease in the level of the aggregates of Bcl10 in the presence of the putative regulatory compound indicates that the compound decreases Bcl10 signal transduction. An increase in the level of the aggregates of Bcl10 in the presence of the putative regulatory compound indicates that the compound increases Bcl10 signal transduction.

In one aspect, the step of detecting includes detecting whether the putative regulatory compound inhibits the translocation of the aggregates of Bcl10 to the site of contact between the cell and the stimulus, wherein such inhibition indicates that the putative regulatory compound is an inhibitor of Bcl10 signal transduction. The step of detecting can also include, but is not limited to, using microscopy to visualize Bcl10 in the cell (e.g., using fluorescent microscopy to visualize Bcl10 in the cell), detecting Bcl10 using an antibody that selectively binds to Bcl10, detecting a recombinant Bcl10 protein expressed by the cell, detecting a Bcl10-reporter fusion protein expressed by the cell, using biochemical extraction of Bcl10 from cells and detection of Bcl10 aggregates by biochemical fractionation techniques, measuring changes in a refractive index of intact cells or biochemical extracts of cells, and measuring changes in the light scatter properties of cells. In one embodiment, the method is performed as a high-throughput assay for screening multiple putative regulatory compounds simultaneously.

In one aspect of this embodiment of the invention, the step of contacting the cell with a putative regulatory compound is performed before the step of culturing the cell with the stimulus. In another aspect, the method further includes a step of detecting whether the putative regulatory compound increases or decreases the translocation of the aggregates of Bcl10 to a site of contact between the cell and the putative stimulus, wherein an increase in translocation indicates an increase in Bcl10 signal transduction and wherein a decrease in translocation indicates a decrease in Bcl10 signal transduction. In another aspect, the method further includes a step of detecting a change in a characteristic of Bcl10 activity selected from the group consisting of a change in the level of Bcl10 expression and a change in the level of phosphorylation of Bcl10 in the cell, wherein a change in the level of Bcl10 expression or a change in the level of Bcl10 phosphorylation in the presence of the putative regulatory compound indicates that the putative regulatory compound regulates Bcl10 signal transduction.

In one aspect of this embodiment of the invention, the cell is a T lymphocyte. For example, the method can include the steps of: (a) culturing a T lymphocyte having a T cell antigen receptor (TCR) with a stimulus that activates the T lymphocyte through the TCR signal transduction pathway; (b) contacting the T lymphocyte with a putative regulatory compound under conditions in which, in the absence of the putative regulatory compound, Bcl10 polymerizes by forming aggregates in the T lymphocyte; and (c) detecting whether the level of the aggregates of Bcl10 in the T lymphocyte increases or decreases in the presence of the putative regulatory compound as compared to in the absence of the putative regulatory compound, wherein an increase or decrease in the level of the aggregates of Bcl10 in the presence of the putative regulatory compound indicates that the compound regulates the Bcl10-mediated signal transduction in the cell.

In another aspect of this embodiment of the invention, the cell is a B lymphocyte. For example, the method can include the steps of: (a) culturing a B lymphocyte having a B cell antigen receptor (BCR) with a stimulus that activates the B lymphocyte through the BCR signal transduction pathway; (b) contacting the B lymphocyte with a putative regulatory compound under conditions in which, in the absence of the putative regulatory compound, Bcl10 polymerizes by forming aggregates in the B lymphocyte; and (c) detecting whether the level of the aggregates of Bcl10 in the B lymphocyte increases or decreases in the presence of the putative regulatory compound as compared to in the absence of the putative regulatory compound, wherein an increase or decrease in the level of the aggregates of Bcl10 in the presence of the putative regulatory compound indicates that the compound regulates the Bcl10-mediated signal transduction in the cell.

BRIEF DESCRIPTION OF THE DRAWINGS OF THE INVENTION

The patent or application file contains at least one drawing executed in color. Copies of this patent or patent application with color drawing will be provided by the Office upon request and payment of the necessary fee.

FIG. 1A is a series of microscopic images showing the antigen-regulated relocalization of Bcl10 to the T cell/APC interface.

FIG. 1B is bar graph showing the quantification of maximal T cell Bcl10 fluorescence intensity data.

FIG. 3B is a line graph showing a quantitative analysis of the redistribution of PKCθ-CFP and Bcl10-YFP at the T cell/APC contact site in response to antigen stimulation.

FIG. 4 is a bar graph showing that the formation of Bcl10 aggregates in response to TCR stimulation is PKC-dependent.

DETAILED DESCRIPTION OF THE INVENTION

Figure 2A:
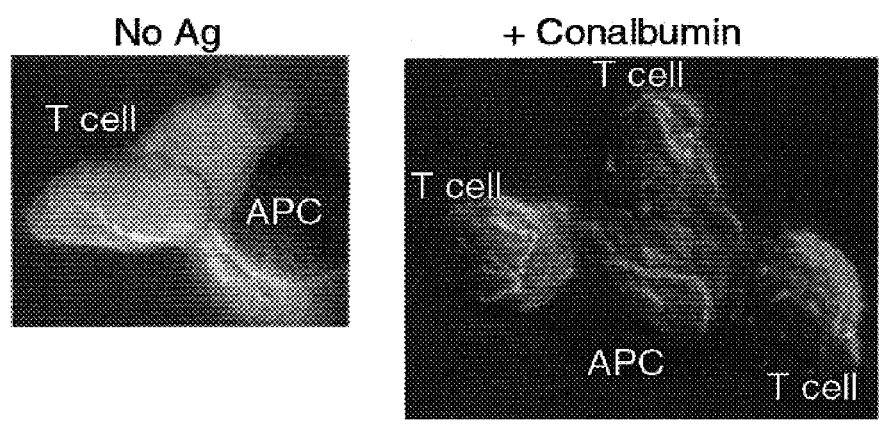
FIG. 2A is a series of microscopic images showing the relocalization of Bcl10 in response to TCR stimulation in T cells expressing Bcl10-YFP.

The present invention generally relates to methods (assays) that are based on a specific characteristic of Bcl10 which is demonstrated to be an important intermediate in a highly significant signaling pathway which includes the activation of the transcription factor NF-κB. Importantly, these methods identify activation of NF-κB in response to activation of a specific signaling pathway via Bcl10. In other words, there are multiple pathways that lead to NF-κB activation, and the methods of the present invention allow the monitoring of one of these pathways, which is a pathway of particular clinical significance. The methods of the invention will allow for the rapid screening of multiple compounds, including small molecule/drug libraries, for compounds that inhibit or enhance Bcl10 activation (and/or Bcl10-mediated cell activation) and thus interfere with or augment, respectively, this particular pathway in the activation of NF-κB. Millions of candidate compounds can rapidly be narrowed down to a relatively small number with the desired activity, followed by further, extensive testing to find the compounds in this post-screen pool that inhibit only the desired pathway.

More specifically, the present inventors have designed an assay for Bcl10-dependent cell activation that is based upon their discovery of a specific polymerization and localization of the Bcl10 protein that is uniquely associated with, and occurs rapidly following, antigen-receptor stimulation of lymphocytes. The microscopic examination of this specific Bcl10 polymerization event allows measurement of Bcl10 activation, and downstream activation of NF-κB, and is generally useful as an early activation marker of cellular activation mediated by Bcl10. More specifically, upon antigen-mediated stimulation of lymphocytes (i.e., activation mediated by the antigen receptor), the Bcl10 protein undergoes a rapid and dramatic redistribution from a diffuse, uniform distribution to punctate and/or long rod-like structures within the cell, which is generally referred to herein as "punctate and filamentous Bcl10 polymerization" or "Bcl10 aggregate formation or polymerization" (described in detail below). Using this activation-induced polymerization of Bcl10, an assay is provided that allows rapid and direct monitoring of Bcl10 polymerization/activation in order to screen for compounds that regulate the Bcl10 signal transduction pathway.

The central supramolecular activation cluster (c-SMAC) comprises a zone of T cell receptor (TCR) enrichment that assembles at a T cell/antigen presenting cell (APC) junction in response to antigen stimulation. The present inventors have demonstrated herein that there is a surprising and unexpected complex relocalization process that brings the protein kinase C, θ isoform (PKCθ) and Bcl10, two intermediates in TCR activation of NF-κB, to the cytoplasmic face of the c-SMAC. Shortly after contact between a T cell and an antigen-loaded antigen presenting cell (APC) or other similar stimulus, PKCθ translocates to the c-SMAC. Within a period of several minutes, enrichment of PKCθ generally reaches its maximal value and then begins to reverse. At approximately the point of maximal PKCθ enrichment at the c-SMAC, Bcl10 begins to coalesce into punctate and filamentous structures (also referred to herein as POLKADOTS, aggregates or clusters) throughout the cytoplasm, often at points distant from the c-SMAC. These punctate and filamentous Bcl10 structures then migrate to the c-SMAC, where they continue to become enriched. The present inventors have also shown that blockade of PKC activity prevents coalescence and phosphorylation of Bcl10, and that NF-κB activation requires both PKC activity and Bcl10 phosphorylation. The inventors have therefore shown that the c-SMAC is a site of sequential enrichment of NF-κB signaling intermediates, and that this enrichment appears to regulate delivery of essential activating signals. These data strongly indicate that the c-SMAC is of unique importance in TCR-regulated activation of NF-κB.

The present inventors' data suggest two probable mechanisms whereby Bcl10 is phosphorylated. The first is that PKCθ constantly shuttles into and away from the c-SMAC, rapidly diffusing throughout the cell. In this model, the enrichment of PKCθ at the c-SMAC reflects a zone of concentration where individual PKCθ molecules reside for a short time before becoming activated and diffusing throughout the cytoplasm to activate Bcl10. This model is supported by the inventors' observation that the enrichment of PKCθ at the c-SMAC is transient, and begins to reverse at about the time POLKADOTS are first evident. The second possibility is that PKCθ activates another kinase, and this second kinase diffuses to distant sites to activate Bcl10, stimulating POLKADOTS formation.

In either case, it is a surprising and unexpected finding that PKCθ and Bcl10 relocalization is so complex. Although both proteins eventually concentrate at the c-SMAC, there is an intermediate period during which Bcl10 POLKADOTS form, and these structures are often distant from the region of PKCθ enrichment at the c-SMAC. These data thus demonstrate that ligand engagement by a transmembrane receptor does not simply result in the clustering of signaling molecules at the cytoplasmic face of the receptor. Rather, other redistribution events distant from the point of receptor engagement are also involved in specific signal transduction processes.

The present invention takes advantage of this surprising discovery to provide a method in which this specific activation characteristic (stimulus-induced Bcl10 aggregation) is used in a rapid screening process for cellular activation and to identify compounds that regulate this cellular activation. Prior to the invention, other researchers had shown the spontaneous or receptor-independent formation of Bcl10 filaments in some cells with highly overexpressed Bcl10. However, the present inventors' data have shown that this is an artifactual result, likely due to the higher levels of overexpression of Bcl10, and this spontaneous filamentation does not provide any useful information regarding the activation state of a cell expressing Bcl10. In contrast, the present inventors have demonstrated that Bcl10 aggregates (punctate and filamentous structures) form rapidly and in a complex relationship with PKCθ localization upon activation of cellular signal transduction, such as through an antigen receptor in a lymphocyte. This specific Bcl10 aggregation in response to an activation stimulus has not been previously described and is an extremely robust and easily detected readout for cellular activation. To the present inventors' knowledge, there is no current reliable assay for the rapid identification of compounds that regulate Bcl10 activation, or cell activation events dependent on Bcl10 activation and until the present invention, a characteristic of Bcl10 that can selectively and rapidly identify Bcl10-dependent activation as a result of antigen receptor-mediated signal transduction (including activation events that trigger this signal transduction pathway downstream of the actual receptor) and thus can selectively identify this specific pathway for NF-κB signaling, had not been described.

Accordingly, one embodiment of the present invention relates to an assay (i.e., a method) for evaluating the activation of Bcl10 in a cell in response to a putative stimulus. Such an assay is useful, for example for the detection and identification of compounds that are effective stimulators of Bcl10-mediated signal transduction, or alternatively, as an activation marker or confirmation of activation in an assay where the stimulator is already known to stimulate the Bcl10-mediated signal transduction pathway (e.g., for further study of the pathway or in an assay where another parameter is being tested). Such an assay can be used to identify the stimulus that is recognized by a particular cell, to identify a cell that recognizes a particular stimulus, to evaluate the effects of modifying culture conditions on a known cell-stimulus interactions, or to evaluate the effects of any other manipulations on such an interaction. In addition, such an assay can be a valuable tool for investigating signal transduction events in any cell, and particularly, in cells such as lymphocytes (e.g., B cells and T cells). The method includes the steps of: (a) contacting an isolated cell having a Bcl10 signal transduction pathway with a putative stimulus; and (b) detecting whether Bcl10 expressed by the cell polymerizes into aggregates in the cell after contact with the putative stimulus, as compared to in the absence of the putative stimulus. The polymerization of Bcl10 into aggregates in the cell indicates Bcl10-mediated activation of the cell.

A second method of the present invention relates to a method for evaluating or identifying a regulatory compound which regulates activation of Bcl10-mediated signal transduction. This method is useful for identifying regulatory compounds that can increase (enhance, upregulate) or decrease (inhibit, reduce, block) Bcl10-mediated (Bcl10-dep3endent) activation, and therefore cellular activation and in some embodiments, Bcl10-mediated activation of NF-κB in a cell. This method includes the use of a known stimulator of Bcl10 activation as a standard against which the regulatory compound is measured. The method includes the steps of: (a) contacting an isolated cell having a Bcl10 signal transduction pathway with a putative regulatory compound and a stimulus, under conditions in which, in the absence of the putative regulatory compound, the stimulus activates the Bcl10 signal transduction pathway such that Bcl10 expressed by the cell polymerizes into aggregates in the cell; and (b) detecting whether the putative regulatory compound increases or decreases the level or localization of the aggregates of Bcl10 in the cell in as compared to in the absence of the putative regulatory compound. An increase or decrease in the level or localization of the aggregates of Bcl10 in the presence of the putative regulatory compound indicates that the compound regulates Bcl10-mediated signal transduction in the cell.

Various aspects of the methods of the invention will be described below. It will be understood that this invention is not limited to the particular methodology, protocols, cell lines, animal species or genera, constructs, or reagents described herein, as such may vary. It is also to be understood that the terminology used herein is for the purpose of describing particular embodiments only, and is not intended to limit the scope of the invention that will be limited only by the appended claims. All technical and scientific terms used herein have the same meaning as commonly understood to one of ordinary skill in the art to which this invention belongs unless clearly indicated otherwise.

As discussed above, B-cell CLL/lymphoma 10 (Bcl10) is encoded by a gene (bcl10) that is involved in the chromosomal translocation t(1;14)(p22;q32) found in mucosa-associated lymphoid tissue lymphoma (MALT lymphoma). Since it was initially described, Bcl10 has been shown to be essential for nuclear factor (NF)-κB activation after lymphocyte antigen receptor stimulation. The nucleic acid and amino acid sequence of Bcl10 is known in different mammalian organisms, including human, rat and mouse. For example, the nucleic acid sequence encoding human Bcl10 can be found in the public databases under Accession No. GI:20336470 and is represented herein as SEQ ID NO:1. SEQ ID NO:1 encodes the human Bcl10 protein represented herein by SEQ ID NO:2. The nucleic acid sequence encoding murine Bcl10 can be found in the public databases under Accession No. GI:6753165 and is represented herein as SEQ ID NO:3. SEQ ID NO:3 encodes the murine Bcl10 protein represented herein by SEQ ID NO:4. The nucleic acid sequence encoding rat Bcl10 can be found in the public databases under Accession No. GI:13786151 and is represented herein as SEQ ID NO:5. SEQ ID NO:5 encodes the rat Bcl10 protein represented herein by SEQ ID NO:6. The knowledge of such sequences, and functional fragments and homologues thereof, are useful, for example, in the provision of recombinant nucleic acid molecules and reporter constructs described herein.

According to the present invention, reference to Bcl10 refers to any Bcl10 protein or a gene or other nucleic acid molecule encoding such protein. Bcl10 can also refer to proteins encoded by allelic variants that have a similar, but not identical, nucleic acid sequence to naturally occurring, or wild-type, sequences. An allelic variant is a gene that occurs at essentially the same locus (or loci) in the genome as the Bcl10 gene, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions).

The first step of the above-identified methods of the present invention includes a step of contacting a putative stimulus (in the case of the method of evaluating the activation of Bcl10 in a cell) or a known stimulus (in the case of the method of identifying a regulatory compound) with an isolated cell having a Bcl10 signal transduction pathway. A stimulus is any compound or other signal that stimulates (induces, initiates, activates, enhances) a process, such as a signal transduction process in a cell.

In one method of the present invention, a cell having a Bcl10 signal transduction pathway is contacted with a putative regulatory compound for regulating Bcl10-mediated signal transduction (and therefore cellular activation which can include activation of NF-κB) in the presence of or absence of a known Bcl10 activator (stimulus). As used herein, the term "regulate" or "regulatory" can be used interchangeably with the term "modulate" or "modulatory". To "regulate" a molecule, a pathway, or a function of Bcl10 or a Bcl10 signal transduction pathway in the present invention refers to specifically controlling, or influencing the activity of such a molecule, pathway, or function, and can include regulation by activation, stimulation, inhibition, alteration or modification of such molecule, pathway or function. Thus, Bcl10 regulation can include upregulating or downregulating Bcl10, and can include regulating a biological event associated with normal Bcl10 signal transduction in a cell (e.g., NF-κB activation, proliferation of a cell, etc.), as long as the regulation particularly impacts the Bcl10 signal transduction pathway (e.g., an event that affects NF-κB activation through a non-Bcl10 signal transduction pathway is not considered to be regulation of Bcl10).

As used herein, the term "putative", when used in connection with reference to a stimulus or another regulatory compound, refers to compounds having an unknown or previously unappreciated regulatory activity (e.g., stimulatory activity) in a particular process. In one embodiment, a putative stimulus can be believed to be an actual stimulus or may even be known to be a stimulus under some conditions, but is being specifically tested for its previously unknown or not-yet-confirmed ability to stimulate Bcl10-mediated activation of a cell in a method of the present invention. Putative stimuli or putative regulatory compounds can include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from molecular diversity strategies (a combination of related strategies allowing the rapid construction of large, chemically diverse molecule libraries), libraries of natural or synthetic compounds, and in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

Synthesis techniques for the production of protein and non-protein compounds, including organic and inorganic compounds are well known in the art. For smaller peptides, chemical synthesis methods are preferred. Such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3–13; Wade et al., 1993, *Australas Biotechnol.* 3(6):332–336; Wong et al., 1991, *Experientia* 47(11–12): 1123–1129; Care et al. 1991, *Ciba Found Symp.* 158:187–203; Plaue et al., 1990, *Biologicals* 18(3):147–157; Bodanszky, 1985, *Int. J. Pept. Protein Res.* 25(5):449–474; or H. Dugas and C. Penney, BIOORGANIC CHEMISTRY, (1981) at pages 54–92, all of which are incorporated herein by reference in their entirety. A compound that is a protein or peptide can also be produced using recombinant DNA technology and methods standard in the art, particularly if larger quantities of a protein are desired.

As used herein, the phrase "signal transduction pathway" or "signal transduction event" refers to at least one biochemical reaction, but more commonly a series of biochemical reactions, that typically involves the interaction of several molecules within a cell and results in a "signal" being transmitted from one molecule to another, ultimately resulting in a cellular response. A signal transduction pathway is usually initiated from the interaction of a cell with a regulatory compound or molecule that causes a change in one or more signal transduction molecules expressed by the cell.

A signal transduction pathway refers to the biochemical relationship between a variety of signal transduction molecules that play a role in the transmission of a signal from one portion of a cell to another portion of a cell. A signal transduction molecule can be any protein, lipid, polynucleotide, or ion involved in a signal transduction pathway, and can be expressed by a cell or come into contact with a cell from an exogenous source. Signal transduction molecules of the present invention include, for example, cell surface receptors and intracellular signal transduction molecules. For example, a signal transduction molecule can include a cell surface receptor, as well as multiple kinases, receptor binding proteins, scaffold proteins and other molecules that allow the transmission of a signal through the cell via a series of biochemical reactions, resulting in a biological response. As used herein, the phrase "cell surface receptor" includes molecules and complexes of molecules capable of receiving a signal and the transmission of such a signal across the plasma membrane of a cell. An example of a "cell surface receptor" of the present invention is the T cell antigen receptor (TCR) or a B cell antigen receptor (BCR). As used herein, the phrase "intracellular signal transduction molecule" includes those molecules or complexes of molecules involved in transmitting a signal from the plasma membrane of a cell through the cytoplasm of the cell, and in some instances, into the cell's nucleus. In the present invention, Bcl10 and PKCθ are examples of intracellular signal transduction molecules, which can also be called simply "signal transduction molecules."

A signal transduction pathway in a cell can be initiated by interaction of a cell with a stimulator that is inside or outside of the cell. If an exterior (i.e. outside of the cell) stimulator (e.g., an MHC-antigen complex on an antigen presenting cell, in the case of a T cell) interacts with a cell surface receptor (e.g., a TCR), a signal transduction pathway can transmit a signal across the cell's membrane, through the cytoplasm of the cell (e.g., through translocation of a variety of molecules, such as Bcl10), and in some instances into the nucleus. If an interior (e.g. inside the cell) stimulator interacts with an intracellular signal transduction molecule, a signal transduction pathway can result in transmission of a signal through the cell's cytoplasm, and in some instances into the cell's nucleus.

Signal transduction can occur through many biochemical reactions, including, but not limited to, the phosphorylation of a molecule, non-covalent allosteric interactions, complexing of molecules, translocation of molecules, the conformational change of a molecule, calcium release, inositol phosphate production, proteolytic cleavage, cyclic nucleotide production, and diacylglyceride production. Typically, signal transduction includes the phosphorylation of one or more signal transduction molecules such as Bcl10.

Reference to a signal transduction pathway by reference to a particular protein or other signal transduction molecule is to refer to a signal transduction pathway in which the referenced protein or molecule plays a specific role (i.e., mediates, participates), and includes at least the referenced protein or molecule, and is typically intended to include one or more other upstream and/or downstream molecules in the pathway. According to the present invention, a Bcl10 signal transduction pathway refers generally to a pathway in which Bcl10 participates in signal transduction events that include other members of the pathway in the cell. Such members include, but are not limited to, receptors (e.g., antigen receptors expressed by a lymphocyte), protein kinase C (PKC) isoforms (particularly PKCθ), caspase recruitment domain (CARD) proteins, CARMA1, the "paracaspase" MALT1, and NF-κB.

Reference to regulating a particular signal transduction pathway (e.g., a Bcl10-mediated signal transduction pathway), refers to regulating the pathway at some point in the pathway, but it need not necessarily indicate that the entire pathway is regulated, or even that the referenced signal transduction molecule is regulated in that specific event. For example, the T cell receptor signal transduction pathway is a complex pathway of signal transduction molecules that, as the name implies, is mediated through the T cell receptor (TCR). It is noted that Bcl10 is a member of the T cell receptor signal transduction pathway and, in the case of a T cell, the TCR is a member of the Bcl10 signal transduction pathway. In this instance, the TCR is the initiating receptor in the signal transduction pathway, which leads to a variety of other signals and branches of the pathway, until various biological responses are induced in the T cell. Therefore, reference to regulating or activating the TCR signal transduction pathway can refer to an action that is performed on the TCR itself, such as contact of the receptor with a stimulator, but it can also refer to a regulatory event that occurs within the TCR signal transduction pathway, but downstream of the actual TCR. By way of example, one can effectively bypass the TCR itself but still activate the TCR signal transduction pathway by using compounds that activate a molecule just downstream of the TCR (i.e., a molecule that the TCR or a molecule that interacts with the TCR upon stimulation would have activated under normal conditions), such as an activator of PKC.

According to the present invention, it is not necessary to know the identity of all of the signal transduction molecules of a specified signal transduction pathway (e.g., a Bcl10 signal transduction pathway) in order to successfully utilize the methods of the present invention. For example, Bcl10 is ubiquitously expressed in most cells, and therefore, one can use any of a variety of cells that are known to endogenously express the signal transduction pathways of the invention (e.g., any lymphocyte, but not limited to a lymphocyte) in the method of the invention. The present inventors have also shown that one can enhance the ability to detect the desired result by overexpression of one or more signaling molecules (e.g., Bcl10) in a cell that endogenously expresses the signal transduction pathway (discussed in detail below). Furthermore, one could construct in a host cell (e.g., by recombinant technology) only a portion of a given pathway that is required to achieve a particular stage within a larger pathway. For example, one could construct a cell that expresses Bcl10 and molecules upstream of Bcl10 that are required for Bcl10-dependent activation (e.g., a cellular receptor, a kinase that phosphorylates Bcl10, etc.). Cells useful in a method of the present invention include any cell that expresses Bcl10, including cells that endogenously express Bcl10 (and therefore have a Bcl10 signal transduction pathway) and/or cells that have been genetically modified (e.g., by recombinant technology) to express Bcl10 and perhaps other members of the Bcl10 signal transduction pathway. The cells useful in the methods of the invention can include virtually any eukaryotic cell that comprises an endogenous and/or genetically engineered Bcl10 signal transduction pathway, including, but not limited to, mammalian cells and yeast cells. In a preferred embodiment, the cell is a lymphocyte, which can include a B lymphocyte and a T lymphocyte, for example. In another preferred embodiment, the cell is a cell that expresses an Fc receptor (FcR) or an NK cell.

According to the present invention, the term "T cell" and "T lymphocyte" can be used interchangeably. Suitable T cells for use in any of the methods or assays of the present invention include any T cell that has a Bcl10 signal transduction pathway (which is believed to include all T cells). Such cells can include normal T cells (e.g., primary lymph node T cells, primary splenic T cells, or T cells from TCR-transgenic mice), T cell lines and T cell clones, as well as T cell hybridomas. A suitable T cell for use in the present invention can also include genetically engineered T cells, such as recombinant cells that have been transformed with, for example, a recombinant molecule encoding Bcl10 and/or a Bcl10 reporter construct, providing that such a genetically engineered cell includes all of the signal transduction molecules necessary to activate Bcl10 according to the present invention (e.g., Bcl10, when activated, must at least form aggregates).

According to the present invention, a T cell receptor (TCR), as described herein, specifically refers to the antigen receptor of a T cell, and includes TCR that include an a and a α chain (αβ T cells) and TCR that include a γ and a δ chain (γδ T cells). It is recognized in the art that there are a variety of other receptors expressed by a T cell which are important in T cell responses and which may or may not be involved directly in the activation of the cell and the signal transduction pathway that includes Bcl10, including, but not limited to, CD3, CD4, CD8, CD28, CTLA-4, CD45, CD43 and Thy-1.

Preferably, a T cell for use in a method or assay of the present invention has a T cell receptor which binds to, or recognizes, an MHC-antigen complex on an antigen presenting cell or provided as a soluble or fusion molecule. An MHC-antigen complex is one known stimulus of a T cell receptor signal transduction pathway. The MHC, or major histocompatibility complex, is a collection of genes encoding glycoproteins called major histocompatibility complex proteins. In vivo, the primary function of an MHC protein is to present antigen in a form capable of being recognized by a TCR. According to the present invention, reference to an "MHC-peptide complex" or an "MHC-peptide molecule", which terms can be used interchangeably, refers to any portion of an MHC protein that forms a functional peptide binding groove and that has a peptide bound to the peptide binding groove. It is well known in the art that the domain organization of class I and class II proteins forms the antigen binding site, or peptide binding groove. A peptide binding groove refers to a portion of an MHC protein that forms a cavity in which a peptide can bind. The conformation of a peptide binding groove is capable of being altered upon binding of an antigenic peptide to enable proper alignment of amino acid residues important for T cell receptor (TcR) binding to the MHC protein and/or peptide. According to the present invention, "a portion" of an MHC chain refers to any portion of an MHC chain that is sufficient to form a peptide binding groove upon association with a sufficient portion of another chain of an MHC protein. In one embodiment, portions of MHC chains suitable to form a peptide binding groove are the portions of MHC chains that are suitable to produce a soluble MHC protein, and particularly include any suitable portion of the extracellular domains of an MHC chain. A soluble MHC protein lacks amino acid sequences capable of anchoring the molecule into a lipid-containing substrate, such as an MHC transmembrane domain and/or an MHC cytoplasmic domain.

For example, a peptide binding groove of a class I protein can comprise portions of the $\alpha_1$ and $\alpha_2$ domains of the heavy chain capable of forming two β-pleated sheets and two α helices. Inclusion of a portion of the β2-microglobulin chain stabilizes the complex. While for most versions of MHC Class II molecules, interaction of the α and β chains can occur in the absence of a peptide, the two chain complex of MHC Class I is unstable until the binding groove is filled with a peptide. A peptide binding groove of a class II protein can comprise portions of the $\alpha_1$ and $\beta_1$ domains capable of forming two β-pleated sheets and two α helices. A first portion of the $\alpha_1$ domain forms a first β-pleated sheet and a second portion of the $\alpha_1$ domain forms a first α helix. A first portion of the $\beta_1$ domain forms a second β-pleated sheet and a second portion of the $\beta_1$ domain forms a second α helix.

An MHC-binding peptide (e.g., an antigenic peptide or T cell epitope) useful in an MHC-peptide complex can comprise any peptide that is capable of binding to an MHC protein in a manner such that the MHC-peptide complex can bind to a T cell receptor (TcR) and, in one embodiment, thereby induce a T cell response. An MHC-binding peptide that binds to an MHC molecule and is recognized, in conjunction with the MHC molecule, by a T cell receptor, is considered to be an antigenic peptide. Examples of MHC-binding peptides can include peptides produced by hydrolysis and most typically, synthetically produced peptides, including randomly generated peptides, specifically designed peptides, and peptides where at least some of the amino acid positions are conserved among several peptides and the remaining positions are random. Preferably, the length of an MHC-binding peptide is from about 5 to about 40 amino acid residues, more preferably from about 6 to about 30 amino acid residues, and even more preferably from about 8 to about 20 amino acid residues, and even more preferably between about 9 and 11 amino acid residues, including any size peptide between 5 and 40 amino acids in length, in whole integer increments (i.e., 5, 6, 7, 8, 9 . . . 40). While naturally MHC Class II-bound peptides vary from about 9–40 amino acids, in nearly all cases the peptide can be truncated to an about 9–11 amino acid core without loss of MHC binding activity or T cell recognition. Peptides used in an MHC-antigen complex can include peptides comprising at least a portion of an antigen selected from a group consisting of autoantigens, infectious agents, toxins, allergens, or mixtures thereof, as well as synthetically produced peptides used to identify antigens recognized by a specific T cell.

A T cell response typically occurs when a TCR recognizes an MHC protein bound to an antigenic peptide, thereby altering the activity of the T cell bearing the TCR. As used herein, a "T cell response" can refer to the activation, induction of anergy, or death of a T cell that occurs when the TCR of the T cell is bound by an MHC-peptide complex or that occurs when the T cell is stimulated by another stimulus (e.g., by superantigen binding to the TCR, by use of a mitogen, such as a phorbol ester or PKC activator). As used herein, "activation" of a T cell refers to induction of signal transduction pathways in the T cell resulting in proliferation of the T cell and/or the production of cellular products (e.g., interleukin-2) by that T cell. "Anergy" refers to the diminished reactivity by a T cell to an antigen. Activation and anergy can be measured by, for example, measuring the amount of IL-2 produced by a T cell after the cell has been activated, by measuring intracellular and/or extracellular calcium mobilization in the T cell, by measuring proliferation of the T cell, and importantly with regard to the present invention, activation can be measured rapidly by detection of Bcl10-dependent activation as described herein. As used herein, "T cell death" or "T cell apoptosis" refers to the permanent cessation of substantially all functions of the T cell.

Known stimuli of T cell receptor signal transduction and activation include, but are not limited to, an antigen presenting cell (APC) expressing an MHC-antigen complex wherein the antigen is bound to an antigen binding site of the MHC; an antibody that selectively binds to and activates the TCR; an antibody that selectively binds to and activates CD3; a purified, soluble MHC-peptide complex; a T lymphocyte mitogen; an activator of protein kinase C (PKC); and a T lymphocyte superantigen. Suitable APCs for use as a stimulus include, but are not limited to macrophages, dendritic cells and B cells (B lymphocytes). Suitable antigen presenting cells will stimulate (i.e., activate) a T cell if the T cell receptor recognizes the MHC-antigen complex (i.e., the T cell receives a first signal through the TCR-MHC-antigen binding), and if the appropriate costimulatory signals are delivered by the APC (i.e., the T cell receives a second signal through the interactions of other T cell-APC proteins). Antibodies that selectively bind to a wide variety of TCRs (including antibodies that bind to a particular chain of the TCR and antiidiotypic antibodies) and antibodies that bind to CD3, as well as methods to use such antibodies to stimulate T cell receptor activation, are well known in the art. Various T lymphocyte mitogens and stimulators of protein kinase C are also well known in the art and include, but are not limited to, PHA, Conconavalin A (ConA), and phorbol esters. A T lymphocyte superantigen binds to at least a portion of the MHC α chain of class II, the β chain of class II, or a combination of the α and β chains of class II, such binding occurring external to the MHC peptide binding groove. A superantigen also binds to at least a portion of a $V_\beta$ domain of a TCR.

According to the present invention, the terms "B cell" and "B lymphocyte" can be used interchangeably, and can include pre-B cells, immature B cells, and mature B cells, including splenic B cells, lymph node B cells, myeloma cells, peripheral blood B cells, bone marrow B cells and B cell hybridomas. A pre-B cell expresses both low levels of surface μ heavy chain and high levels of cytoplasmic μ heavy chain. An immature B cell expresses both light chains and μ heavy chains as surface IgM molecules (i.e., mIgM). Finally, mature, naive B cells express both mIgM and mIgD. Hybridomas refer to hybrid cell lines comprising myeloma cells (tumor cells capable of being maintained in tissue culture but do not produce immunoglobulin) fused with, for example, a spleen cell capable of producing an immunoglobulin molecule.

Reference to a "B cell antigen receptor" or "BCR" is intended to reference the B cell antigen receptor, which includes a membrane immunoglobulin (mIg) antigen binding component, or a biologically active portion thereof (i.e, a portion capable of binding a ligand and/or capable of associating with a transducer component), and transducer Ig-α and Ig-β components, or biologically active portions thereof (i.e., a portion capable of transducing an intracellular signal and/or capable of associating with an extracellular ligand binding portion).

Aggregation of the BCR by multivalent antigen initiates transphosphorylation of the Ig-α and Ig-β ITAM motifs and activation of receptor-associated kinases (for review see DeFranco, 1997; Kim et al., 1993; Kurosaki, 1997). Phosphorylated ITAMs recruit additional effectors such as PI3-K, PLC-γ and members of the Ras/MAPK pathway. These signaling events are responsible for B cell proliferation, and increased expression of activation markers such as MHC class II and CD86, that are required to prime the B cell for subsequent interactions with $T_h$ cells.

Known stimuli of B cell receptor signal transduction and activation include, but are not limited to, an antibody that selectively binds to and activates the BCR; an activator of protein kinase C (PKC); a phorbol ester; antibodies that selectively bind to and activate transmembrane forms of IgM, IgD, IgG, IgA or IgE; antibodies that selectively bind to and activate the immunoglobulin-associated signaling molecules Ig-α or Ig-β; and polyvalent ligands for IgM, IgD, IgG, IgA or IgE. Polyvalent ligands for IgM, IgD, IgG, IgA or IgE include, but are not limited to, polyvalent cognant antigen, lectins that bind immunoglobulin, and compounds that aggregate surface immunoglobulin.

Reference herein to an "Fc receptor" or "FcR" refers to one or more members of a family of highly related receptors that specifically bind to the Fc portion of immunoglobulin (Ig). FcR can also be referred to herein as immunoglobulin Fc receptors or Ig Fc receptors (Ig FcR). These receptors have major roles in normal immunity and resistance to infection and provide the humoral immune system with a cellular effector arm. Receptors have been defined for each of the immunoglobulin classes and as such are defined by the class of Ig of which they bind (i.e. Fc gamma receptor (FcγR) bind gamma immunoglobulin (IgG), Fc epsilon receptor (FcεR) bind epsilon immunoglobulin (IgE), Fc alpha receptor (FcαR) bind alpha immunoglobulin (IgA)). Among the FcγR receptors, three subfamily members have been defined; FcγRI, which is a high a affinity receptor for IgG; FcγRII, which are low affinity receptors for IgG that avidly bind to aggregates immune complexes; and FcγRIII, which are low affinity receptors that bind to immune complexes. These receptors are highly related structurally but perform different functions. FcγR are expressed on most hematopoietic cells (e.g., monocytes, macrophages, neutrophils, eosinophils, platelets and B lymphocytes). FcεR are expressed on mast cells, basophils and eosinophils.

Reference herein to an NK cell receptor (or NK receptor) refers to a receptor that is expressed by natural killer (NK) cells and that is associated with the activation of the NK cell, such as by binding to a molecule on another cell (e.g., an FcR bound or expressed by another cell, a stress-induced molecule). NK receptors can include killer-activating receptors, for example. Natural killer (NK) cells are identified by their ability to kill certain lymphoid tumor cell lines in vitro without the need for prior immunization or activation. In vivo, NK cells play a role in innate immunity by providing early protection from a range of pathogens.

In certain embodiments, a cell used in the methods and assays of the present invention is a genetically engineered cell, such as a cell that has been transfected with at least one heterologous nucleic acid sequence. Such a nucleic acid molecule can encode a T cell receptor or a B cell receptor, for example, or any molecules of a Bcl10 signal transduction pathway, including Bcl10. In one embodiment, a genetically engineered cell has been transfected with a recombinant nucleic acid molecule encoding a Bcl10 protein. Such a cell can include a cell that also endogenously expresses Bcl10. A genetically engineered cell can include more than one heterologous nucleic acid sequence. Genetic engineering of a cell can be accomplished using molecular genetic techniques, and particularly including recombinant technology. Such techniques are well known in the art and are generally disclosed for cells, for example, in Sambrook et al., 1989, *Molecular Cloning: A Laboratory Manual*, Cold Spring Harbor Labs Press. The reference Sambrook et al., ibid., is incorporated by reference herein in its entirety.

According to the present invention, an isolated nucleic acid molecule is a nucleic acid molecule that has been removed from its natural milieu (i.e., that has been subject to human manipulation) and can include DNA, RNA, or derivatives of either DNA or RNA, including cDNA. As such, "isolated" does not reflect the extent to which the nucleic acid molecule has been purified. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. Reference to a gene (e.g., a Bcl10-encoding gene) includes all nucleic acid sequences related to a natural (i.e. wild-type) gene, such as regulatory regions that control production of the protein encoded by that gene (such as, but not limited to, transcription, translation or post-translation control regions) as well as the coding region itself. Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on protein biological activity.

Preferably, a nucleic acid molecule encoding a signal transduction molecule such as Bcl10 is transfected into a host cell as a recombinant nucleic acid molecule. A recombinant nucleic acid molecule typically comprises a recombinant vector and an isolated nucleic acid molecule as described herein. A recombinant vector is an engineered (i.e., artificially produced) nucleic acid molecule that is used as a tool for manipulating a nucleic acid sequence of choice and/or for introducing such a nucleic acid sequence into a host cell. The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell. The entire vector can remain in place within a host cell, or under certain conditions, the plasmid DNA can be deleted, leaving behind the desired nucleic acid molecule. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

Typically, a recombinant nucleic acid molecule includes at least one nucleic acid molecule operatively linked to one or more expression control sequences, including transcription control sequences and translation control sequences. According to the present invention, the phrase "operatively linked" refers to linking a nucleic acid molecule to an expression control sequence (e.g., a transcription control sequence and/or a translation control sequence) in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced. Recombinant nucleic acid molecules of the present invention can also contain additional regulatory sequences, such as translation regulatory sequences, origins of replication, and other regulatory sequences that are compatible with the recombinant cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells. In microbial systems, the term "transformation" is used to describe an inherited change due to the acquisition of exogenous nucleic acids by the microorganism and is essentially synonymous with the term "transfection." However, in animal cells, transformation has acquired a second meaning which can refer to changes in the growth properties of cells in culture (described above) after they become cancerous, for example. Therefore, to avoid confusion, the term "transfection" is preferably used with regard to the introduction of exogenous nucleic acids into animal cells, including human cells, and is used herein to generally encompass transfection of animal cells and transformation of microbial cells, to the extent that the terms pertain to the introduction of exogenous nucleic acids into a cell. Therefore, transfection techniques include, but are not limited to, transformation, chemical treatment of cells, particle bombardment, electroporation, microinjection, lipofection, adsorption, infection and protoplast fusion.

A recombinant cell is preferably produced by transforming a host cell as described above with one or more recombinant molecules, each comprising one or more nucleic acid molecules operatively linked to an expression vector containing one or more expression control sequences.

In one embodiment of the present invention, a cell useful in the present methods has been selected to have a level of Bcl10 expression (endogenous and/or recombinant) in the level of Bcl10 expression is such that spontaneous filaments do not form or form infrequently. Spontaneous filaments of Bcl10 are defined herein as Bcl10 filaments or aggregates that form in the absence of activation of Bcl10 signal transduction. Spontaneous filaments have occasionally been observed as an artifact certain cells in vitro and are not associated with the activation state of the cell (e.g., is receptor-independent). It is a preferred embodiment that very high levels of overexpression of Bcl10 be avoided (such as is typically seen in transient transfections). However, in both normal and genetically modified cells, one can readily select cells that have a low level or no detectable level of Bcl10 aggregation in the absence of specific stimulation by producing cell lines with appropriate levels of Bcl10 expression (e.g., by and/or by using various subcloning techniques to identify suitable cells.

For example, it will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts. In addition, subcloning techniques to select for cells with the desired genotype and or phenotype are well known in the art, and an example of subcloning to select a cell with preferred levels of Bcl10 expression is provided in the Examples.

The above described methods, in one aspect, involve contacting cells with stimulus and/or a putative regulatory compound being tested for a sufficient time to allow for interaction of the stimulus and/or the putative regulatory compound with the cell such that if the compound is a stimulus or other regulatory molecule, the Bcl10 signal transduction pathway is activated. The conditions under which the cell (or cell lysate in some embodiments) of the present invention is contacted with a putative regulatory compound, such as by mixing, are any suitable culture or assay conditions in which the cell can transduce a normal signal (i.e., activation of Bcl10) if essentially no regulatory compound is present (other than a suitable stimulus). Effective culture conditions include, but are not limited to, effective media, bioreactor, temperature, pH and oxygen conditions that permit cellular activation and growth to occur. An effective medium refers to any medium in which a given host cell is typically cultured. Such medium typically comprises an aqueous medium having assimilable carbon, nitrogen and phosphate sources, and appropriate salts, minerals, metals and other nutrients, such as vitamins. Cells of the present invention can be cultured in a variety of containers including, but not limited to, tissue culture flasks, test tubes, microtiter dishes, and petri plates. Such culturing conditions are also within the skill in the art.

Cells are contacted with aputative regulatory compound under conditions which take into account the number of cells per container contacted, the concentration of putative regulatory compound(s) administered to a cell, the incubation time of the putative regulatory compound with the cell, and the concentration of compound administered to a cell. Determination of effective protocols can be accomplished by those skilled in the art based on variables such as the size of the container, the volume of liquid in the container, conditions known to be suitable for the culture of the particular cell type used in the assay, and the chemical composition of the putative regulatory compound (i.e., size, charge etc.) being tested. In one embodiment, an amount of putative regulatory compound(s) comprises between about 1 nM to about 10 mM of putative regulatory compound(s) per well of a 96-well plate.

The period of contact with the compound being tested can be varied depending on the type of compound being tested, the culture conditions, and on the result being measured, and can be determined by one of skill in the art. In general, the method of the present invention is a rapid assay requiring a short contact period. Activation of Bcl10 can be measured in a cell in the first several minutes after stimulation, as shown in the Examples. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to evaluating the assay. The incubation time for growth of cells can vary but is sufficient to allow for the upregulation or downregulation of Bcl10-dependent activation in a cell. It will be recognized that shorter incubation times are preferable because compounds can be more rapidly screened. A preferred incubation time is between about 1 minute to about 12 hours, with very short time periods (e.g., 1 to 30 minutes) being particularly preferred.

According to the present invention, when a putative regulatory compound is screened in the presence of a known stimulus of Bcl10-dependent activation in the cell, the putative regulatory compound can be contacted with the cell prior to, simultaneously with, or after contact of the cell with the known stimulus. In addition, a suitable control is preferably included as a means of comparison in the assay. Typically, one suitable control for a method of the present invention is a cell having a Bcl10 signal transduction pathway, and preferably a cell of the same type as the test cell, wherein the control cell is cultured in the absence of the putative stimulus. In this manner, Bcl10 aggregation (described in detail below) in the test cell is always compared to an unstimulated control, wherein one can readily determine a background level of Bcl10 aggregation (if any) and then identify putative stimuli which cause a statistically significant increase in Bcl10 aggregates as compared to the unstimulated control. In the case of the method of identifying a putative regulatory compound, a suitable control includes both a cell cultured in the absence of any stimulus or putative regulatory compound (e.g., a background control), and also a cell that is contacted with a known stimulus (a known activator of Bcl10-dependent signaling) in the absence of the putative regulatory compound. If the putative regulatory compound is a cell activation inhibitor, the level (amount, number, density) of Bcl10 aggregates will be less than the level of Bcl10 aggregates that form in the stimulated control. A putative regulatory compound that enhances cell activation may cause an increased level of formation of Bcl10 aggregates as compared to the positive and the negative control. Although this readout (Bcl10 aggregate formation) can be combined with the detection of other endpoints (discussed below), it is not necessary to combine this readout with any other Bcl10 characteristics, since Bcl10 aggregate formation as described by the present inventors is by far the most robust and easily detected readout yet shown for Bcl10-mediated activation.

To be identified as a positive regulatory compound, a compound increases or decreases Bcl10 aggregation as compared to the established control by an amount that is statistically significant (i.e., with at least a 95% confidence level, or $p<0.05$). Preferably, detection of at least about a 10% change in aggregation level in the test sample as compared to the control level results in a positive identification. More preferably, detection of at least about a 30% change, and more preferably, detection of at least about a 50% change, and more preferably at least about a 70% change, and more preferably at least about a 90% change, or any percentage change between 5% and higher in 1% increments (i.e., 5%, 6%, 7%, 8% . . . ) in Bcl10 aggregation level the test sample as compared to the control level results in a positive identification of a regulatory compound. In one embodiment, a 1.5 fold change, or more preferably, detection of at least about a 3 fold change, and more preferably at least about a 6 fold change, and even more preferably, at least about a 12 fold change, and even more preferably, at least about a 24 fold change, or any fold change from 1.5 up in increments of 0.5 fold (i.e., 1.5, 2.0, 2.5, 3.0 . . . ) in Bcl10 aggregation level the test sample as compared to the control level results in a positive identification of a regulatory compound.

In the methods of the present invention, after the cell is contacted with a putative stimulus, the method includes a step detecting whether Bcl10 expressed by the cell polymerizes into aggregates in the cell, as compared to in the absence of the putative stimulus. In the method where the cell is contacted with a known stimulus and a putative regulatory compound, the step includes detecting whether the level of Bcl10 aggregate formation increases or decreases as compared to in the absence of the putative regulatory compound. In either method, the detection of an increase in the level of Bcl10 aggregate formation in the test cell as compared to the negative control cell (or as compared to a positive control cell), indicates that the putative stimulus is an actual stimulus or that the putative regulatory compound is a stimulator of Bcl10-dependent activation of the cell. Detection of a decrease in the level of Bcl10 aggregate formation in the test cell as compared to a positive control that has been stimulated with a known stimulator indicates that a putative regulatory compound is an inhibitor of Bcl10-dependent cellular activation. Detection of no change in the level of Bcl10 aggregate formation as compared to the control will depend on the control. In the case of a negative control (i.e., no stimulus), detection of no change indicates that the putative regulatory compound or stimulus does not stimulate Bcl10-dependent cellular activation. In the case of a positive control (i.e., in the presence of a known stimulus), detection of no change indicates that the putative regulatory compound is not an inhibitor of Bcl10-dependent cellular activation, and also indicates that the compound is not a potent or detectable enhancer of Bcl10-dependent cellular activation.

Although several characteristics of Bcl10-dependent activation are described herein that can be used in a method of the present invention, the present invention is directed to a unique characteristic of Bcl10-dependent activation that has been discovered by the present inventors, and relates to the rapid and dramatic redistribution of Bcl10 in a cell upon activation of the cell through the antigen receptor signal transduction pathway. As discussed above, the method of the present invention makes use of the dramatic change upon cellular activation in the form and distribution of Bcl10 from a diffuse, uniform distribution within the cell to punctate and/or long rod-like structures within the cell. According to the present invention, activated Bcl10 can be identified by its presence as "punctate and filamentous" structures in a cell, which are generally referred to herein as Bcl10 aggregates. An aggregate is defined as being formed of separate units in a cluster, or formed by a collection of Bcl10 proteins in to a mass or cluster. Polymerization of proteins into punctate and filamentous structures will be understood by those of skill in the art. As used herein, Bcl10 polymerized aggregates can be also referred to as Punctate and Oligomeric Killing or Activating Domains Transducing Signals (POLKADOTS), Bcl10 clusters, or Bcl10 punctate and filamentous structures. Bcl10 aggregation that is useful as a readout in the present invention is related to the stimulation of the Bcl10-dependent signal transduction in the cell and thus is directly correlated with activation. Spontaneous filamentation of Bcl10 that may occur in some cells as an artifact can be filtered out as background by use of appropriate controls in the assay, or can be eliminated altogether by manipulation and/or selection of cells for low or no spontaneous filament formation.

Bcl10 aggregates can be detected by any suitable means, including using optical, electric or microscopic techniques, as well as biochemical and chemical techniques. Detection of a level of aggregation can include any quantitative or qualitative measurement of aggregation in a cell and will depend on the particular technique used. For example, detecting a level of aggregation may include counting aggregates, determining the mass of aggregates, and most frequently will include quantifying aggregates using a detectable label, perhaps in conjunction with an aggregate separation technique. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

In a preferred embodiment, the step of detecting is performed using microscopy to visualize Bcl10 aggregates in the cell. Microscopic visualization techniques are well known in the art and include many highly sophisticated techniques, whereby one can visualize Bcl10 aggregation in a single cell and/or over time, including in real time. Microscopy can include, but is not limited to, fluorescent microscopy, such as immunofluorescent microscopy. Microscopic techniques for visualizing and qualitatively or quantitatively measuring Bcl10 aggregation are described in the Examples.

The step of detecting can also include any technique that utilizes an antibody that selectively binds to Bcl10 for detection. According to the present invention, the phrase "selectively binds to" refers to the ability of an antibody, antigen binding fragment or other antigen binding compound to preferentially bind to a specified protein. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art.

In one embodiment, the step of detecting comprises using biochemical extraction of Bcl10 from cells and detection of Bcl10 aggregates by biochemical fractionation techniques. Such biochemical fractionation techniques include, but are not limited to, gel electrophoresis and gradient centrifugation.

In another embodiment, the step of detecting Bcl10 aggregates comprises measuring changes in a refractive index of intact cells or biochemical extracts of cells. Such techniques include using surface plasmon resonance, chemiluminescence, phosphorescence, or any other method that measures changes in refractive index of intact cells or biochemical extracts of cells.

In yet another embodiment, the step of detecting Bcl10 aggregates comprises measuring changes in the light scatter properties of cells. Such techniques include using flow cytometry, fluorescence activated cell sorting (FACS) or any other method that measures changes in the light scatter properties of cells.

In one embodiment, the step of detecting Bcl10 aggregation can include detecting a recombinant Bcl10 protein expressed by the cell. This embodiment has been discussed above, and can be achieved by any of the techniques useful for detecting Bcl10 as discussed herein. In one preferred embodiment, the test cell is transfected with a recombinant nucleic acid encoding a Bcl10-reporter fusion protein that is expressed by the cell and detected using the appropriate technique. In this embodiment, the read-out can use a Bcl10 promoter, or can also include a portion of the Bcl10 gene, which is linked (fused) to any of several reporter constructs encoding a detectable reporter, which are then introduced into cells by any of several established transfection or infection methods. The level of Bcl10-reporter aggregation is determined in the presence of the putative regulatory compound and compared to the level of expression in the absence of the compound. Suitable reporter genes include, but are not limited to, alkaline phosphatase, horseradish peroxidase, luciferase, cyan fluorescent protein (CFP), blue fluorescent protein (BFP), red fluorescent protein (DsRFP), green fluorescent protein (GFP), yellow fluorescent protein (YFP) (see Examples). Particularly suitable reporter genes include those that encode a protein that is detectable by microscopy.

Although the use of detection of Bcl10 stimulus-dependent aggregation is sufficient to perform the methods of the present invention, other characteristics of Bcl10 activation can be use in addition to detecting Bcl10 aggregation to identify cell activation stimuli and other cell activation regulators. For example, as discussed previously, the present inventors have demonstrated that there is a surprising and unexpected complex relocalization process that brings the protein kinase C, θ isoform (PKCθ) and Bcl10 to the cytoplasmic face of the c-SMAC. Shortly after contact between a T cell and an antigen-loaded antigen presenting cell (APC) or other similar stimulus, PKCθ translocates to the c-SMAC. Within a period of several minutes, enrichment of PKCθ generally reaches its maximal value and then begins to reverse. At approximately the point of maximal PKCθ enrichment at the c-SMAC, Bcl10 begins to coalesce aggregates throughout the cytoplasm, often at points distant from the c-SMAC. These Bcl10 aggregates then migrate to the c-SMAC, where they continue to become enriched. The present inventors have also confirmed that Bcl10 phosphorylation is required for Bcl10-dependent signal transduction. The timing for translocation of Bcl10 aggregates to the c-SMAC can be expressed in minutes, for example, and is described in detail in the Examples.

Therefore, in one embodiment, the method of the present invention can further comprise detecting translocation of the aggregates of Bcl10 to a site of contact between the cell and the putative stimulus, the translocation being further indicative of Bcl10-mediated activation of the cell. If desired, one can also analyze the status of PKCθ translocation and activation or any other PKC isoform in conjunction with Bcl10 aggregation and/or translocation to evaluate the activation state of the cell. The site of contact is the site where a signal transduction molecule at the beginning of a signal transduction pathway (e.g., a receptor) contacts the stimulus that initiates signal transduction. Translocation of a molecule represents a change in the physical location of the molecule from its location in a resting (i.e., non-activated) cell to another site, such as the site of contact between a signal transduction molecule and its stimulus. For example, the binding of a T cell receptor to an MHC-antigen complex forms a site or point of contact between the T cell and the antigen presenting cell. Such a site of contact between a T cell and an antigen presenting cell is an antigen-specific interaction, as opposed to a random cell-cell contact. As a result of this antigen-specific interaction, various signal transduction molecules downstream of the TCR are activated and some, such as Bcl10, translocate to the site of contact, thus indicating that the T cell has been activated and can proliferate. If no antigen-specific site of contact is formed, the translocation of such molecules will not occur, therefore serving as a further indicator that the T cell is not activated and will not proliferate. Since Bcl10 translocation is separated temporally from the initial aggregation of Bcl10 and from the translocation of PKC, for example, one may evaluate Bcl10 aggregation and translocation over time in connection with other established controls (e.g., PKC translocation), to further assess and/or confirm cellular activation.

In one embodiment, the method of the invention can also include a step of detecting whether there is a change (regulation, modification) in the level of Bcl10 expression in the cell in the presence of the putative stimulus as compared to the level of Bcl10 expression in the absence of the putative stimulus, change in Bcl10 expression being further indicative Bcl10-mediated activation of the cell. The level of expression of Bcl10 will change upon Bcl10-mediated cell activation. Bcl10 expression will be either upregulated or downregulated, as compared to the unstimulated control, depending on the cell type and possibly depending on the degree of stimulation. For example, in naive T cells, the level of Bcl10 protein increases in response to previous stimulation, whereas in previously stimulated T cells and T cell clones, in response to high levels of stimulation, there is a decrease in the level of Bcl10 protein expression, which, without being bound by theory, the inventors believe is due to a cellular proteolytic process. As used herein, the term "expression", when used in connection with detecting the expression of Bcl10 or another molecule, can refer to detecting transcription of the gene and/or to detecting translation of the protein encoded by the gene. To detect expression of a gene or protein refers to the act of actively determining whether a gene or protein is expressed or not. This can include determining whether the expression is upregulated as compared to a control, downregulated as compared to a control, or unchanged as compared to a control. Expression of transcripts and/or proteins is measured by any of a variety of known methods in the art. For RNA expression, methods include but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene. Measurement of translation of a protein include any suitable method for detecting and/or measuring proteins from a cell or cell extract. Such methods include, but are not limited to, immunoblot (e.g., Western blot), enzyme-linked immunosorbant assay (ELISA), radioimmunoassay (RIA), immunoprecipitation, immunohistochemistry, immunofluorescence, fluorescence activated cell sorting (FACS) and immunofluorescence microscopy.

In yet another embodiment, the method can include the step of detecting whether Bcl10 is phosphorylated in the cell, the phosphorylation of Bcl10 being further indicative of Bcl10-mediated activation of the cell. Phosphorylation can be measured using techniques that are standard in the art. Detection of Bcl10 phosphorylation is described in the Examples.

In a most preferred embodiment, the method of the present invention includes any high-throughput assay for screening multiple putative regulatory compounds simultaneously. For example, using an antigen receptor activation of Bcl10 as an example, such an assay could use a stable cell line expressing a Bcl10-fluorescent protein fusion, and would preferably be a human T or B cell line. Cells would be distributed into replicate wells of microtiter plates, and then pretreated with candidate regulatory compounds (putative regulatory compounds). Stimulation of the cell line with an appropriate antigen or antigen analog (e.g., an anti-antigen receptor antibody) would then be used to trigger Bcl10 polymerization. After a specified period of time (e.g., several minutes) the cells would be chemically fixed, to preserve the cells in their activated state, allowing analysis over an extended time period. Each well would then be examined to determine whether or not Bcl10 polymerization (aggregation) had occurred, which could easily be accomplished by an automated system designed to discriminate aggregated Bcl10 from diffuse Bcl10. Wells in which there was no Bcl10 aggregation would identify compounds which block Bcl10 aggregation. These compounds would then be subjected to further, more detailed activity screens as desired.

The present invention also includes various assay kits that are designed to facilitate any of the methods described herein, and can be comprised of standard reagents that are available in the art. For example, an assay kit useful in the method of the present invention can include one or more of: reagents for the detection of Bcl10 (e.g., an antibody, including an antibody or binding portion thereof having a detectable label); cells useful for detecting regulation of Bcl10 signal transduction as described herein, including cells expressing endogenous Bcl10 and cells that have been genetically engineered to express Bcl10; reagents for the detection of a control marker; and reagents needed to prepare and develop the assay samples, such as reagents or substrates for the preparation of samples and/or development of the assay such that microscopic analysis can be performed.

Also included in the present invention are therapeutic compositions formulated from any stimuli or other regulatory compounds for the regulation of Bcl10-dependent signal transduction that are identified using the present methods, as well as methods of therapeutic treatment using such compounds. For example, compounds identified by the present methods can be used to treat a variety of diseases and conditions, including, but not limited to, autoimmune diseases or diseases with a likely immunopathogenic component (e.g., type I diabetes, rheumatoid arthritis, inflammatory bowl diseases (e.g., Crohn's disease), psoriasis, multiple sclerosis, systemic lupus erythamatosus), prevention of rejection of transplanted organs or grafts, and cancer, including leukemias and lymphomas, and particularly MALT lymphoma and the autoimmune conditions that predispose individuals to development of MALT lymphoma (including Sjogren's syndrome, Hashimoto's thyroditis, and gastric inflammation in response to chronic *H. pylori* infection). In addition, compounds identified by the present methods can readily serve as lead compounds for the development of improved compounds having enhanced abilities to regulate the Bcl10-dependent signal transduction in cells.

The following experimental results are provided for purposes of illustration and are not intended to limit the scope of the invention.

EXAMPLES

Materials and Methods

The following Materials and Methods were used in Examples 1–5 described below.

Cell Culture

D10-IL2 (henceforth referred to as D10) is an IL-2 dependent subclone of the CD4+ T cell clone D10 (16), maintained as described (17). Primary T cell blasts were prepared by stimulation of spleen and lymph node cells with 100 µg/ml plate-bound anti-TCRβ for 48 hr, with IL-2 added for the final 24 hr of stimulation. CH12H-$2^k$ B cells and CHb H-$2^b$ B cells (18) were maintained as described previously (17).

Retroviral Constructions and Infections

Murine PKCθ was fused to a C-terminal linker (GRVELGR; SEQ ID NO:7) followed by GFP or CFP (19), modified by mutations that improve folding at 37° C. (20). Two I.M.A.G.E. expressed sequence tag (EST) clones encoding murine Bcl10 were purchased (2123397 and 3026026; ResGen). Clone 3026026 was used for PCR amplification of Bcl10, adding the C-terminal linker GR, which was then fused to the previously described modified YFP gene (17). The PKCθ-CFP and Bcl10-YFP gene fusions were cloned into the retroviral vectors pEneo and pEhyg (21), respectively. Retroviral infection and cell line production were as described (17).

Microscopy

Fluorescent and Nomarski images were acquired on an Olympus IX70 inverted microscope (Olympus America, Inc.) or a Zeiss Axiovert 200M inverted microscope (Carl Zeiss, Inc.) using a 100X plan-apochromat oil objective. The microscope was controlled by a TILLvisTRAC imaging system, driven by TILLvisION 4.0 software (TILL Photonics, GmbH). Excitation light was provided by a Polychrome IV monochromator (TILL Photonics, GmbH). Dichroic mirrors and excitation filters appropriate for each fluorophore were purchased from Chroma.

Western Blotting

T cells were stimulated with 100 µg/ml plate-bound anti-TCRβ. Cell lysates were prepared on ice using 1X Laemmli buffer, followed by sonication. For immunoprecipitations, 5×10$^6$ cells were lysed for 1 hr on ice in 360 µL of a buffer consisting of 0.5% NP40, 0.5% deoxcholate, 20 mM Tris, pH 7.6, 250 mM NaCl, 3 mM EDTA, 3 mM EGTA, 1 mM PMSF, 20 µg/ml aprotinin, 100 µg/ml leupeptin, 1 mM Na$_3$VO$_4$, 10 mM NaF, and 1 mM DTT. Nuclei were removed by centrifugation, and lysates were incubated with polyclonal rabbit anti-Bcl10 antibody (Santa Cruz Biotechnology) for 2–3 hr at 4° C. and then for 1 hr at 4° C. with Protein A sepharose. Lysates and immunoprecipitates were separated by SDS-PAGE and blotted onto nitrocellulose. Proteins were detected by monoclonal antibodies against Bcl10 (Santa Cruz Biotechnology), and PKCθ (BD/Translabs), and polyclonal antibodies against phospho-IκBα, anti-phospho-PKCθ/Thr538 (Cell Signaling Technologies), and actin (Santa Cruz Biotechnology). For phosphatase treatment, immunoprecipitates were incubated for 45 min at 30° C. with 400 U of λ-phosphatase (New England Biolabs), according to the instructions of the manufacturer.

Detailed Microscopy and Image Processing Methodology

For fixed cell imaging, T cell conjugates were formed, mounted on coverslips, paraformaldehyde fixed, and stained with fluorophore-conjugated antibodies (Molecular Probes, Inc.) as described previously (16). For each fluorescent wavelength, z-stacks of 50 xy-planes separated by 0.3 µm were acquired, and stacks were digitally deconvolved using a constrained-iterative algorithm. TILLvisION software was used to convert z-stacks into xy projection images, by retaining only the maximal pixel value for each xy coordinate across the z-dimension. Displayed images are representative of multiple experiments in which at least 20 different conjugates were observed for each experimental condition.

For live cell imaging, antigen-loaded B cells were plated in Delta T dishes mounted in a Bioptechs heated stage set to 37° C. After B cells settled on the bottom of the dish, D10 T cells were added. Fluorescent imaging was initiated as soon as T cells were observed in close proximity to B cells. For each xy-plane, 200 ms exposures were taken at 430 nm (for detection of PKCθ-CFP) and at 510 nm (for detection of Bcl10-YFP). Each acquisition time point consisted of z-stacks of thirty xy-planes separated by 0.5 µm, which took 9 s to complete. The fluorescent acquisition was followed immediately by a single infrared exposure of 1 s and a 50 s delay, so that each acquisition cycle took 1 min. Forty such 1 min cycles were performed. Fluorescent images at each time point were assembled into projection images, as described above. Each set of projection images and infrared images were combined into a 40-image series. Displayed images are representative of multiple experiments, and have been reproduced with two independently produced polyclonal cell lines, and multiple subclones from these lines. Fifteen live cell interactions of 30 to 40 minutes have been analyzed in detail.

To correct data for photobleaching, the mean fluorescence intensity (MFI) was computed for a whole T cell at each time point. Background fluorescence (BF) was subtracted from each value and relative fluorescence (RF) was calculated for each time point by dividing all the values by the initial t=0 MFI (As expected for a photobleaching process, the resulting bleach curves follow a first-order kinetic when data are plotted as log(MFI) vs time). A correction curve was then constructed by taking the inverse of the RF (iRF) at each time point. Two TILLvisION macros were written to correct image series for photobleaching (unpublished). The first macro subtracted BF+5 from each xy coordinate (the arbitrary value of 5, which is about 10% of the average background fluorescence, is added to BF to account for pixel-to-pixel fluctuations in background), resulting in a background-corrected image series. The second macro multiplied each pixel by the appropriate iRF for each time point, creating a photobleaching-corrected series.

The two corrected fluorescent image series and one infrared series were then combined into a single RGB color series, with red representing PKCθ-CFP fluorescence, green representing Bcl10-YFP fluorescence and blue representing the infrared images. In some cases, fluorescent image series were also represented using a pseudocolor-intensity color palette. Image series were exported from TILLvisION as AVI movies. Movie frame rates were changed as needed, using the program AVIedit (AM Software).

For the quantitative analyses (e.g., FIG. 3B) regions were drawn and the mean fluorescence intensity of the bounded area was calculated using functions in TILLvisION. Specifically, in each frame, a region was drawn around the border (i.e., the plasma membrane) of the T cell. A second region was drawn to demarcate the T cell/APC contact, which we defined as the maximal area of PKCθ enrichment over the 40 min experiment (this manually defined contact region was kept the same size and shape in every frame, but was moved as necessary in the x and y directions to compensate for any movement of the T cell). The mean fluorescence in each region was calculated at every time point. After correcting for photobleaching (see above), the fold-enrichment at the contact region was calculated by dividing the mean fluorescence intensity of each contact region by the whole-cell mean fluorescence intensity.

Example 1

The following example demonstrates the redistribution of endogenous Bcl10 in response to specific antigen stimulation.

The inventors sought to establish whether Bcl10, like PKCθ, might be recruited to the c-SMAC in response to specific antigen-loaded APC. Recent work using antibody capping (22) or antibody-coated beads (4) has shown that Bcl10 can be recruited to the cytoplasmic face of the engaged TCR, but no analysis of Bcl10 localization to SMACs in a T cell/APC interaction model has been reported. The inventors produced T cell blasts from mice transgenic for a TCR specific for an ovalbumin peptide (Ova 323–339) bound to $IA^b$ (OTII mice (23)). OTII T cell blasts were incubated for 45 minutes with CHb APC that had been loaded with either no antigen (FIG. 1A; CHb+No Antigen), or with 10 μg/ml of the ovalbumin peptide, OVA 323–339 (FIG. 1A; CHb+Ovalbumin). T cell/APC conjugates were detected by immunofluorescence microscopy, using monoclonal antibodies directed against Bcl10, PKCθ and CD4 (FIG. 1A). Referring to FIG. 1A, images of T cell/APC conjugates are arranged as follows (left to right): Nomarski, anti-Bcl10 (red), anti-PKCθ (green), anti-CD4 (blue) and an overlay of the three fluorescent images.

In the absence of specific antigen, no enrichment of PKCθ was seen at the T cell/APC interface (FIG. 1A, top two rows) and T cell Bcl10 was observed throughout the cytoplasm. In contrast, in T cells stimulated by specific antigen-loaded CHb APC, PKCθ became enriched at the region of contact between the T cell and the APC. Bcl10 was preferentially relocalized to a region of the T cell that was at or near the T cell/APC interface (FIG. 1A, bottom two rows). The amount of Bcl10 in the region of enrichment near the T cell/APC contact in ovalbumin-stimulated cells was much greater than the most intensely staining regions in the no antigen controls. The mean maximal anti-Bcl10 fluorescence intensity of the enriched regions of the antigen-stimulated T cells was 7-fold higher than the maximal T cell anti-Bcl10 fluorescence of the no antigen controls (FIG. 1B; error bars representing SEM). Referring to FIG. 1B, note that the 7-fold increase in maximal Bcl10 enrichment of ovalbumin-stimulated cells relative to unstimulated cells underestimates the average increase, since 2/8 ovalbumin-stimulated cells displayed Bcl10 fluorescence above the maximal detection limit (65,534).

These results thus show that endogenous T cell Bcl10 both relocalizes to and becomes substantially enriched at the T cell/APC interface in response to specific antigen stimulation.

Example 2

The following example demonstrates that fluorescent protein fusions of Bcl10 recapitulate the behavior of endogenous Bcl10.

In order to study antigen-mediated relocalization of Bcl10 in more detail, the inventors constructed a fluorescent protein fusion between Bcl10 and yellow fluorescent protein (YFP). For these experiments, the $CD4^+$ T cell clone D10 was used, which is specific for a conalbumin peptide bound to $IA^k$, and D10 cells were infected with a Bcl10-YFP retrovirus. In these cells, Bcl10-YFP was diffusely localized throughout the cell, and this distribution was unchanged when the cells were conjugated with CH12 APC in the absence of antigen (FIG. 2A, left panel, "No Ag"). However, a dramatic redistribution of Bcl10-YFP into punctate and filamentous structures was observed when these T cells were conjugated with conalbumin-loaded CH12 APC (FIG. 2A, right panel, "+Conalbumin", 500 μg/ml Conalbumin). Referring to FIG. 2A, the fluorescent image is overlayed on the Nomarski image. The Bcl10-YFP fusion protein is therefore dramatically relocalized in response to TCR stimulation.

In some cells, the punctate pattern was very similar to that observed for endogenous Bcl10 (compare T cell at far right of FIG. 2A, right panel, to antigen-stimulated T cells in FIG. 1a), and the Bcl10 filaments observed in a subset of cells (e.g., T cell at far left of FIG. 2A, right panel) were more similar to the "spontaneous" filaments of Bcl10 that have been reported to occur in a subset of Bcl10-transfected HeLa cells (24). Further characterization of D10 subclones (data not shown) has shown that filamentous structures occur in TCR-stimulated cells with the highest level of Bcl10-YFP expression, suggesting that the more punctate structures most accurately represent the structures formed by endogenous Bcl10 in non-transduced, antigen-stimulated T cells.

Figure 2B:
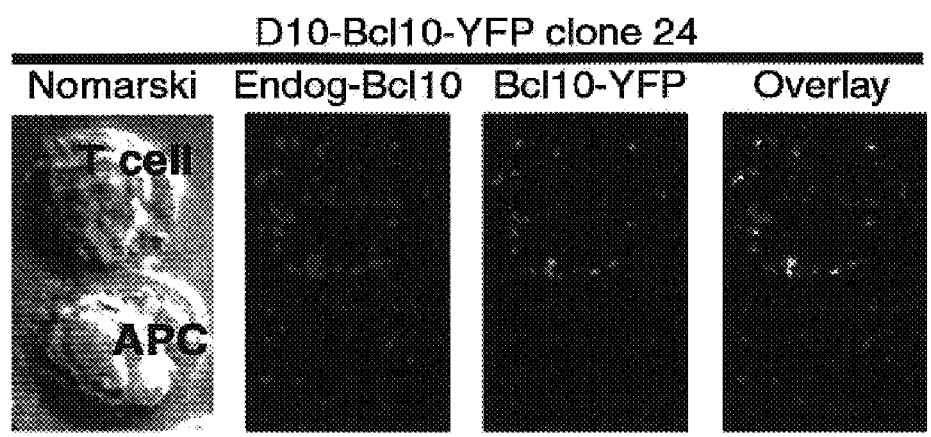
FIG. 2B is a series of microscopic images showing the relocalization of both endogenous Bcl10 and recombinant Bcl10-YFP in T cells in response to TCR stimulation of T cells.

To establish that endogenous Bcl10 and the fluorescent fusion protein undergo equivalent redistribution, D10 T cells that express Bcl10-YFP were subjected to limiting dilution cloning, and a subclone (cl.24) was identified with low, uniform expression of Bcl10-YFP. Western blotting showed that the level of Bcl10-YFP expression was 10% lower than the level of endogenous Bcl10 in this subclone (data not shown), and an antibody staining experiment demonstrated that endogenous Bcl10 and the fluorescent protein fusion redistribution in an indistinguishable manner in response to antigen stimulation (FIG. 2B). Referring to FIG. 2B, microscopy images of D10-Bcl10-YFP cl.24 cells conjugated to CH12 B cells (pre-loaded with 250 μg/ml of conalbumin protein) are arranged as follows (left to right): Nomarski, anti-Bcl10 (red), anti-GFP (green), and an overlay of the fluorescent images. The anti-GFP monoclonal antibody JL-8 (BD/Clontech) was employed to boost the YFP signal in this cell line for detection by fluorescence microscopy. This experiment demonstrated both that the fluorescent protein tag does not affect relocalization of the Bcl10 fusion protein, and that the monoclonal anti-Bcl10 antibody is indeed highly specific for the Bcl10 protein.

To further characterize the mechanism of redistribution of Bcl10, the G78R mutation was introduced into the Bcl10-

Figure 2C:
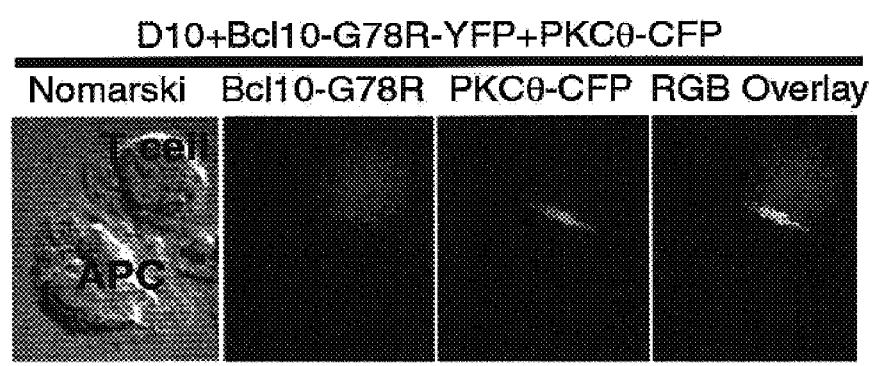
FIG. 2C is a series of microscopic images showing that the introduction of the G78R mutation into the Bcl10-YFP CARD completely blocked the antigen driven redistribution of Bcl10-YFP, without influencing the antigen-stimulated redistribution of PKCθ.

YFP CARD. This mutation is known to inactivate the Bcl10 CARD, and it has previously been shown to prevent the formation of "spontaneous" Bcl10 filaments in HeLa cells (23). Referring to FIG. 2C, D10 T expressing the CARD mutant Bcl10-G78R-YFP and PKCθ-CFP were incubated with CH12 B cells (APC) in the presence of 250 μg/ml of conalbumin protein for 30 min. The images are arranged as follows (left to right): Nomarski, Bcl10-G78R-YFP (red), PKCθ-CFP (green), and an overlay of the fluorescent images. In these experiments, this mutation completely blocked the antigen driven redistribution of Bcl10-YFP, without influencing the antigen-stimulated redistribution of PKCθ (FIG. 2C). Thus, Bcl10 redistribution requires a functional Bcl10 CARD.

The punctate and filamentous structures formed by Bcl10 in antigen stimulated T cells are quite similar to oligomeric filamentous structures, called DEFs (death effector filaments), which are formed by specific mediators of apoptosis (25,26). Interestingly, Bcl10 and its tightly associated binding partner, a caspase-like protein called MALT1 (27), contain protein interaction motifs of the death domain-fold family (28, 29), also found in mediators of cell death. Thus, these punctate and filamentous structures may represent a higher-order signaling complex common to death domain-fold protein activators of caspases and caspase-like proteins. Because these cellular domains are visually quite similar, and because they both appear to perform a similar function (i.e., signal transduction), the present inventors have named these structures POLKADOTS (Punctate and Oligomeric Killing or Activating Domains Transducing Signals).

Example 3

The following example demonstrates that redistribution of Bcl10 is not dependent upon cytoskeletal filaments.

Because TCR stimulation causes formation of Bcl10 POLKADOTS, which sometimes adopt a filamentous appearance, the inventors decided to examine the possibility that Bcl10 clustering might involve cytoskeletal filaments. To circumvent the problem that many cytoskeletal inhibitors also impair T cell/APC conjugate formation, D10 T cells were activated with phorbol ester (PMA), a stimulator of PKC. Specifically, in these experiments, D10 T cells infected with retroviruses encoding PKCθ-CFP and Bcl10-YFP received no pre-treatment, 2 hr pretreatment with 10 μg/ml nocodazole, or 1 hr pretreatment with 2 μg/ml latrunculin A. Cells then received either no treatment or were incubated for 20 min with 10 ng/ml PMA.

Indeed, PMA stimulation of D10 T cells expressing PKCθ-CFP and Bcl10-YFP led to the translocation of PKCθ-CFP to the cell membrane (data not shown) and the formation of Bcl10-YFP POLKADOTS (data not shown). In PMA-stimulated cells pretreated with nocodazole, microtubules were disrupted, as indicated by the diffuse cytoplasmic distribution of tubulin. Cells pretreated with latrunculin A also did not appear to have reduced levels of Bcl10-YFP POLKADOTS (data not shown). Thus, the formation of Bcl10 POLKADOTS does not depend upon the presence of either microtubules or actin microfilaments.

To assess potential associations between POLKADOTS and intermediate filaments, a CFP-vimentin fusion protein was introduced into D10 T cells expressing Bcl10-YFP (lymphocyte intermediate filaments are primarily composed of vimentin (30), and CFP-vimentin fusion proteins have been shown to be functional (31)). These T cells were incubated with APC either in the absence or presence of specific antigen (data not shown). In unstimulated cells, CFP-vimentin intermediate filaments showed the expected uropod localization (32) (data not shown), and Bcl10-YFP showed the expected diffuse cellular distribution. In antigen-stimulated cells, the CFP-vimentin re-oriented towards the site of TCR clustering, as has been previously described (30), and Bcl10-YFP formed POLKADOTS (data not shown). Because Bcl10-YFP POLKADOTS and CFP-vimentin frequently did not colocalize, the data strongly suggest that POLKADOTS are not associated with intermediate filaments, although association with a minority population of intermediate filaments cannot be ruled out.

Bcl10 POLKADOTS are thus an oligomeric structure distinct from cytoskeletal filaments. It thus seems most likely that POLKADOTS are de novo oligomers formed in T cells as the result of a TCR-dependent post-translational modification of Bcl10 or a Bcl10-associated protein.

Example 4

The following example demonstrates that Bcl10 POLKADOTS relocalize to the c-SMAC, following PKCθ redistribution.

Figure 3A:
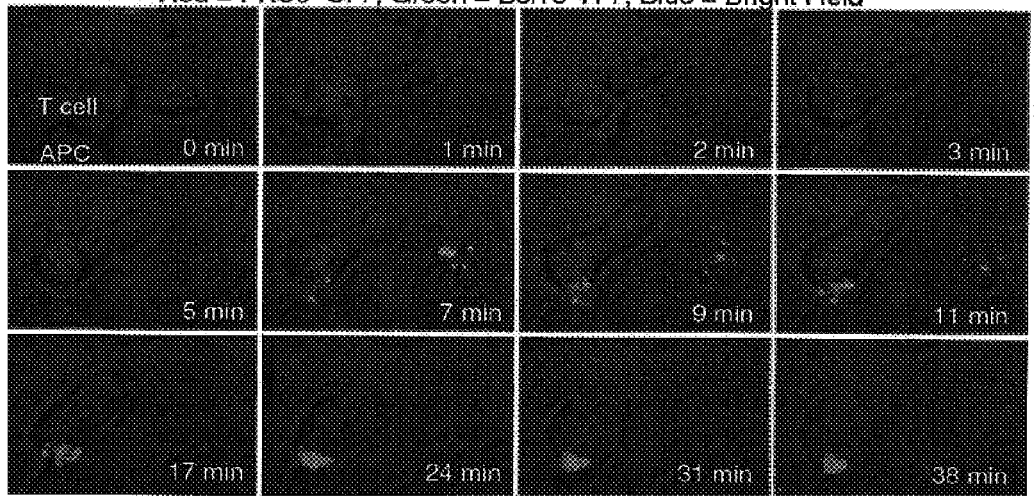
FIG. 3A is a series of microscopic images taken from a live cell imaging analysis of PKCθ-CFP and Bcl10-YFP redistribution in response to antigen stimulation.

Since TCR stimulation causes the relocalization of both PKCθ (33) and Bcl10 (see Examples 1 and 2 above), the potential kinetic relationship between the redistribution of these two molecules was investigated. D10 T cells expressing both PKCθ-CFP and Bcl10-YFP were mixed with conalbumin-loaded CH12 B cells, and the redistribution of PKCθ-CFP and Bcl10-YFP was monitored in seven-parameter live cell imaging experiments. In these image series, red represents PKCθ-CFP, green represents Bcl10-YFP, and blue is an infrared/bright field image. Z-series data were collected once a minute for 40 minutes, and selected frames are shown in FIG. 3A. Referring to FIG. 3A, frames at the indicated times are shown; the complete 39 frame series is from a movie not shown here. An additional cell, which appears to have been activated and then separated from the activating APC, is seen at the right of the T cell/APC conjugate beginning at 7 min.

FIG. 3A shows that within the first minute following initial contact between the D10 T cell and the CH12 B cell, PKCθ translocated to the T cell/APC interface. Several minutes later, Bcl10-YFP began to assemble into POLKADOTS at many sites in the cytoplasm. Over time, many of the Bcl10-YFP POLKADOTS were rearranged so that they became condensed at the T cell/APC interface, at the area of PKCθ-CFP enrichment. Thus PKCθ-CFP and Bcl10-YFP cluster in an overlapping region at the c-SMAC.

In an additional example of the experiment shown in FIG. 3A, early T cell/APC interaction was observed, in which PKCθ-CFP has already translocated to the interface between the cells, but Bcl10-YFP has not yet formed POLKADOTS (data not shown). In this experiment, Bcl10-YFP POLKADOTS were initially observed at approximately the 3 min time point, scattered throughout the cytoplasm. The Bcl110-YFP POLKADOTS became redistributed over time to the contact between the T cell and the APC, overlapping with the site of enrichment of PKCθ. Additionally, the intensity of Bcl10-YFP enrichment at the T cell/APC contact increased over time, apparently due both to the continued redistribution of cytoplasmic Bcl10-YFP to existing POLKADOTS and to the recruitment of additional POLKADOTS to this site.

These data were quantitatively analyzed, which is reflected in FIG. 3B. Referring to FIG. 3B, the points show relative enrichment of PKCθ-CFP (rectangles) and Bcl10-YFP (circles) at the T cell/APC contact over time. The relative enrichment of each fluorescent protein in the whole cell is defined as 1 (dashed line). As shown in FIG. 3B, during minutes 0–2, the enrichment of PKCθ-CFP at the contact increased to a level approximately 3-fold over the mean fluorescence intensity for the entire cell. This period of enrichment was followed by a reversal of this translocation during minutes 2–39. In contrast, Bcl10-YFP enrichment at the contact did not begin until POLKADOTS began to form, and this enrichment continued throughout the time course. Thus, PKCθ translocation to the T cell/APC interface precedes Bcl10 POLKADOTS formation and the enrichment of Bcl10 at the T cell/APC interface.

Example 5

The following example demonstrates that TCR stimulation causes PKC-dependent phosphorylation of Bcl10.

The inventors next investigated whether Bcl10 redistribution reflects biochemical modification of Bcl10. Interestingly, a recent study of CARMA1 mutant mice has shown that CARMA1 is required for PMA-dependent Bcl10 phosphorylation in B cells (7). However, there has been no demonstration of TCR-dependent Bcl10 phosphorylation in T cells. D10 T cells expressing PKCθ-CFP and Bcl10-YFP were stimulated for 60 minutes with no antibody or with anti-TCRβ, and western blotting analyses of Bcl10-YFP and endogenous Bcl10 were performed to detect phosphorylated forms of the proteins (data not shown). These data show that Bcl10-YFP and Bcl10 exist single predominant isoforms (approx 60 kDa and 30 kDa, respectively) in unstimulated D10 T cells, whereas much of the 60 kDa and 30 kDa isoforms were converted to two more slowly migrating forms during 60 min of anti-TCR stimulation. λ-phosphatase treatment of immunopreciptated Bcl10-YFP and endogenous Bcl10 from anti-TCR stimulated D10 T cells converted the slowly migrating forms to the most rapidly migrating form (data not shown), demonstrating that the slowly migrating forms are phosphorylated.

To determine whether TCR-dependent phosphorylation of Bcl10 requires PKC activity, the D10 T cells expressing PKCθ-CFP and Bcl10-YFP were stimulated with anti-TCR, following pre-treatment for 30 minutes with either 0.1% DMSO or 2 μM bisindolylmaleimide (bisindo), a specific protein kinase C inhibitor. Bisindo treatment completely blocked formation of phosphorylated Bcl10-YFP (data not shown). Furthermore, Bcl10-YFP phosphorylation was closely associated with activation of NF-κB (as assessed by monitoring phosphorylation of IκBα), and both signaling events were blocked by treatment with bisindo (data not shown). Additionally, the kinetics of phosphorylation of Bcl10-YFP matched the kinetics of POLKADOTS formation in response to this immobilized anti-TCR antibody treatment (data not shown). Notably, the activation of the ERK MAP kinases was not blocked, but was partially inhibited by bisindo, in agreement with published data (34). These data thus demonstrate that TCR-dependent phosphorylation of Bcl10 and concomitant activation of NF-κB are PKC-dependent signaling events.

Figure 5:
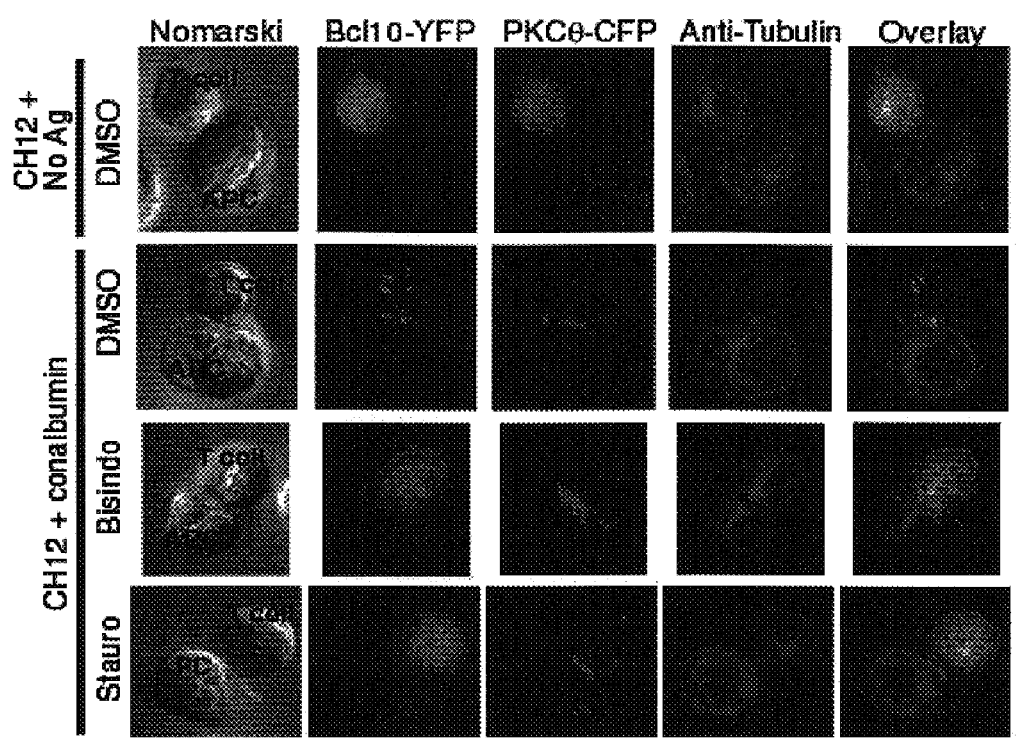
FIG. 5 is a series of microscopic images showing that PKCθ translocation occurs in the absence of PKC catalytic activity and that Bcl10 aggregate formation is inhibited by PKC inhibitors.

The inventors next examined whether formation of Bcl10 POLKADOTS is PKC-dependent (FIG. 4 and FIG. 5). D10 T cells expressing Bcl10-YFP were incubated with CH12 B cells with no antigen, or with conalbumin-loaded CH12 B cells (100 μg/ml conalbumin). Some of the antigen-stimulated samples were also pre-treated for 30 minutes with bisindolylmaleimide (2 μM), and some were pre-treated for 30 minutes with the broad-spectrum protein kinase inhibitor staurosporine (stauro, 100 nM). Cells were fixed after 20 minutes and examined by fluorescence microscopy. For each group, >200 T cells were counted, and percentages with and without POLKADOTS were determined. As shown in FIG. 4, antigen stimulation resulted in formation of Bcl10-YFP POLKADOTS in over 80% of the cells. In contrast, POLKADOTS formation was blocked by treatment with stauro or bisindo. Thus, both TCR-stimulated Bcl10-YFP POLKADOTS formation and Bcl10 phosphorylation require PKC activity.

In a second experiment, D10 T cells expressing PKCθ-CFP and Bcl10-YFP were pretreated for 30 min with 0.1% DMSO, 2 μM bisindolylmaleimide (Bisindo) or 100 nM staurosporine (Stauro). CH12 B cells that had been pre-incubated with no antigen or with 250 μg/ml conalbumin protein were then added. Cells were fixed after 30 min and examined by fluorescence microscopy. Referring to FIG. 5, for each treatment group, a Nomarski image is followed by three fluorescent images, showing Bcl10-YFP (green), PKCθ-CFP (blue), and anti-Tubulin (red). The final column (far right) is an overlay of the three fluorescent panels. FIG. 5 also shows that Bcl10 POLKADOTS formation was blocked by treatment with stauro or bisindo, and that PKCθ translocation occurs in the absence of PKC catalytic activity.

Finally, to determine the dependence of NF-κB activation on Bcl10 phosphorylation, the inventors examined IκBα phosphorylation in D10 T cells expressing the G78R CARD mutant of Bcl10. In these experiments, D10 T cells expressing PKCθ-CFP and Bcl10-YFP or PCKθ-CFP and Bcl10-G78R-YFP were stimulated with 100 μg/ml plate-bound anti-TCRβ. Proteins were detected by western blotting, and relative amounts of the phosphorylated forms of IκBα were detected for each time point. The results (data not shown) demonstrated that the CARD mutant of Bcl10 does not become phosphorylated in response to anti-TCR stimulation, and it acts as a dominant-negative, blocking TCR-dependent IκBα phosphorylation. Bcl10 phosphorylation is thus a necessary intermediate in TCR activation of NF-κB.

Without being bound by theory, the present inventors propose that the existence of two distinct reorganization events that bring two different mediators of TCR activation of NF-κB to the c-SMAC provides evidence that the c-SMAC is of functional importance in the regulation NF-κB. Although SMACs may not be involved in the delivery of certain very early signals from the TCR (35), a consensus view is emerging, which postulates that SMACs exist for the purpose of providing a stable signaling platform for the lengthy series of biochemical signals originating from antigen stimulation of the TCR (12, 36, 37). The present inventors propose that the c-SMAC regulates activation of a subset of TCR-controlled signaling pathways, which require continued TCR signaling following SMAC organization (38). Based on the inventors' observation of sequential localization of NF-κB signal transducers to the c-SMAC, it is proposed herein that TCR activation of NF-κB is "validated" at multiple steps, via delivery of signals from the engaged TCR to critical NF-κB signaling intermediates that traffic to the c-SMAC in a spatially organized and temporally ordered manner. Such validation would ensure that the NF-κB signal, which commits a T cell to S-phase, is only delivered to the nucleus upon sustained TCR engagement by antigen.

References

Each reference cited below and elsewhere herein is incorporated herein by reference in its entirety.

1. Boothby et al. (1997) *J Exp Med* 185, 1897–907.
2. Ruland et al. (2001) *Cell* 104, 33–42.

3. Sun et al. (2000) *Nature* 404, 402–7.
4. Egawa et al. (2003) *Curr Biol* 13, 1252–1258.
5. Newton and Dixit (2003) *Curr Biol* 13, 1247–51.
6. Hara et al. (2003) *Immunity* 18, 763–75.
7. Jun et al. (2003) *Immunity* 18, 751–62.
8. Ruefli-Brasse et al. (2003) *Science*, published online Oct. 23, 2003, 10.1126/science.1090769.
9. Monks et al. (1998) *Nature* 395, 82–6.
10. Grakoui et al. (1999) *Science* 285, 221–7.
11. Dustin and Cooper (2000) *Nat Immunol* 1, 23–9.
12. Krummel and Davis (2002) *Curr Opin Immunol* 14, 66–74.
13. Kupfer et al. (1990) *J Mol Cell Immunol* 4, 317–25.
14. Wang et al. (2002) *Nat Immunol* 3, 830–5.
15. McAllister-Lucas et al. (2001) *J Biol Chem* 276, 30589–97.
16. Kaye et al. (1983) *J Exp Med* 158, 836–56.
17. Schaefer et al. (1999) *Immunity* 11, 411–21.
18. Haughton et al. (1986) *Immunol Rev* 93, 35–51.
19. Heim and Tsien (1996) *Curr Biol* 6, 178–82.
20. Crameri et al. (1996) *Nat Biotechnol* 14, 315–9.
21. Schaefer et al. (2001) *Anal Biochem* 297, 86–93.
22. Gaide et al. (2002) *Nat Immunol* 3, 836–43.
23. Barnden et al. (1998) *Immunol Cell Biol* 76, 34–40.
24. Guiet and Vito (2000) *J Cell Biol* 148, 1131–40.
25. Perez and White (1998) *J Cell Biol* 141, 1255–66.
26. Siegel et al. (1998) *J Cell Biol* 141, 1243–53.
27. Uren et al. (2000) *Mol Cell* 6, 961–7.
28. Fairbrother et al. (2001) *Protein Sci* 10, 1911–8.
29. Martinon et al. (2001) *Curr Biol* 11, R118–20.
30. Dellagi and Brouet (1982) *Nature* 298, 284–6.
31. Yoon et al. (2001) *J Cell Biol* 153, 503–16.
32. Brown et al. (2001) *J Immunol* 166, 6640–6.
33. Monks et al. (1997) *Nature* 385, 83–6.
34. Puente et al. (2000) *J Immunol* 165, 6865–71.
35. Lee et al. (2002) *Science* 295, 1539–42.
36. Dustin and Chan (2000) *Cell* 103, 283–94.
37. Delon and Gerrnain (2000) *Curr Biol* 10, R923–33.
38. Freiberg et al. (2002) *Nat Immunol* 3, 911–7.
39. Cambier (1995) *Immunol. Today* 16, 110.
40. DeFranco (1997) *Curr. Opin. Immunol.* 9, 296–308.
41. Kim et al. (1993) *Immun. Rev.* 132, 125–46.
42. Kurosaki (1997) *Curr. Opin. Immunol.* 9, 309–18.

It is apparent that modifications and adaptations of the embodiments of the invention disclosed herein will occur to those skilled in the art. It is to be expressly understood, however, that such modifications and adaptations are within the scope of the present invention, as set forth in the following claims.

---

What is claimed is:

1. A method for evaluating activation of Bcl10 in a cell in response to a putative stimulus:
   a) contacting an isolated cell having a Bcl10 signal transduction pathway with a putative stimulus; and
   b) detecting whether Bcl10 expressed by the cell polymerizes into punctate and filamentous structures in the cell after contact with the putative stimulus as compared to in the absence of the putative stimulus, wherein the polymerization of Bcl10 into punctate and filamentous structures in the cell indicates Bcl10-mediated activation of the cell.

2. The method of claim 1, wherein the step of detecting comprises using microscopy to visualize Bcl10 in the cell.

3. The method of claim 1, wherein the step of detecting comprises using fluorescent microscopy to visualize Bcl10 in the cell.

4. The method of claim 1, wherein the step of detecting comprises detecting Bcl10 using an antibody that selectively binds to Bcl10.

5. The method of claim 1, wherein the step of detecting comprises detecting a recombinant Bcl10 protein expressed by the cell.

6. The method of claim 1, wherein the step of detecting comprises detecting a Bcl10-reporter fusion protein expressed by the cell.

7. The method of claim 1, wherein the cell is a lymphocyte expressing an antigen receptor, and wherein the polymerization of Bcl10 into punctate and filamentous structures in the cell in the presence of the putative stimulus indicates activation of the cell through an antigen receptor-associated, Bcl10 signal transduction pathway.

8. The method of claim 1, further comprising detecting translocation of the punctate and filamentous structures of Bcl10 to a site of contact between the cell and the putative stimulus, the translocation being further indicative of Bcl10-mediated activation of the cell.

9. The method of claim 1, further comprising detecting whether there is a change in the level of Bcl10 expression in the cell in the presence of the putative stimulus as compared to the level of Bcl10 expression in the absence of the putative stimulus, a change in Bcl10 expression being further indicative Bcl10-mediated activation of the cell.

10. The method of claim 1, further comprising detecting whether Bcl10 is phosphorylated in the cell, the phosphorylation of Bcl10 being further indicative of Bcl10-mediated activation of the cell.

11. The method of claim 1, wherein the cell is a T lymphocyte.

12. The method of claim 11, wherein the T lymphocyte is selected from the group consisting of a primary lymph node T lymphocyte, a primary splenic T lymphocyte and a T lymphocyte from a transgenic mouse.

13. The method of claim 11, wherein the T lymphocyte is a T lymphocyte clone or a T lymphocyte hybridoma.

14. The method of claim 11, wherein the method comprises:
   a) culturing a T lymphocyte expressing a T cell receptor (TCR) with a putative stimulus for activating the T lymphocyte through the TCR signal transduction pathway; and
   b) detecting whether Bcl10 expressed by the T lymphocyte polymerizes into punctate and filamentous structures in the T lymphocyte in the presence of the putative stimulus as compared to in the absence of the putative stimulus, wherein the polymerization of Bcl10 into punctate and filamentous structures in the T lymphocyte indicates Bcl10-mediated activation of the T lymphocyte.

15. The method of claim 14, wherein the putative stimulus is selected from the group consisting of: an antigen presenting cell expressing a major histocompatibility complex (MHC)-antigen complex wherein the antigen is bound to an antigen binding site of the MHC; an antibody that selectively binds to and activates the TCR; an antibody that selectively binds to and activates CD3; a purified, soluble MHC-peptide complex; a T lymphocyte mitogen; an activator of protein kinase C (PKC); and a T lymphocyte superantigen.

16. The method of claim 14, wherein the step of contacting comprises contacting the T lymphocyte with an antigen presenting cell expressing an MHC-antigen complex, wherein the antigen is bound to an antigen binding site of the MHC, wherein, if the TCR binds to the MHC-antigen complex, an antigen-specific site of contact between the T lymphocyte and the antigen presenting cell is formed.

17. The method of claim 14, wherein the putative stimulus is selected from the group consisting of: an antibody that selectively binds to and activates the TCR and an antibody that selectively binds to and activates CD3.

18. The method of claim 14, wherein the putative stimulus is a T lymphocyte mitogen selected from the group consisting of PHA and Conconavalin A (ConA).

19. The method of claim 14, wherein the putative stimulus is a phorbol ester.

20. The method of claim 1, wherein the lymphocyte is a B lymphocyte.

21. The method of claim 20, wherein the B lymphocyte is selected from the group consisting of a primary B lymphocyte and a B lymphocyte from a transgenic mouse.

22. The method of claim 20, wherein the B lymphocyte is a B lymphocyte hybridoma.

23. The method of claim 20, wherein the method comprises:
   a) contacting a B lymphocyte expressing a B cell antigen receptor (BCR) with a putative stimulus for activating the B lymphocyte through the BCR; and b) detecting whether Bcl10 expressed by the B lymphocyte polymerizes into punctate and filamentous structures in the B lymphocyte in the presence of the putative stimulus as compared to in the absence of the putative stimulus, wherein the polymerization of Bcl10 into punctate and filamentous structures in the B lymphocyte indicates Bcl10-mediated activation of the lymphocyte.

24. The method of claim 23, wherein the putative stimulus is selected from the group consisting of: an antibody that selectively binds to and activates the BCR and an activator of protein kinase C (PKC).

25. The method of claim 23, wherein the putative stimulus is a phorbol ester.

26. The method of claim 23, wherein the putative stimulus is selected from the group consisting of:
a) antibodies that selectively bind to and activate transmembrane forms of IgM, IgD, IgG, IgA or IgE;
b) antibodies that selectively bind to and activate the immunoglobulin-associated signaling molecules Ig-α or Ig-β; and
c) polyvalent ligands for IgM, IgD, IgG, IgA or IgE.

27. The method of claim 26, wherein the polyvalent ligands for IgM, IgD, IgG, IgA or IgE are selected from the group consisting of: polyvalent cognant antigen, lectins that bind immunoglobulin, and compounds that aggregate surface immunoglobulin.

28. A method to identify a regulatory compound which regulates activation of Bcl10-mediated signal transduction, comprising:
a) contacting an isolated cell having a Bcl10 signal transduction pathway with a putative regulatory compound and a stimulus, under conditions in which, in the absence of the putative regulatory compound, the stimulus activates the Bcl10 signal transduction pathway such that Bcl10 expressed by the cell polymerizes into aggregates in the cell; and
b) detecting whether the putative regulatory compound increases or decreases the level of the aggregates of Bcl10 in the cell in as compared to in the absence of the putative regulatory compound, wherein an increase or decrease in the level of the aggregates of Bcl10 in the presence of the putative regulatory compound indicates that the compound regulates Bcl10-mediated signal transduction in the cell.

29. The method of claim 28, wherein a decrease in the level of the aggregates of Bcl10 in the presence of the putative regulatory compound indicates that the compound decreases Bcl10 signal transduction.

30. The method of claim 28, wherein an increase in the level of the aggregates of Bcl10 in the presence of the putative regulatory compound indicates that the compound increases Bcl10 signal transduction.

31. The method of claim 28, wherein the step of detecting comprises detecting whether the putative regulatory compound inhibits the translocation of the aggregates of Bcl10 to the site of contact between the cell and the stimulus, wherein such inhibition indicates that the putative regulatory compound is an inhibitor of Bcl10 signal transduction.

32. The method of claim 28, wherein the step of detecting is performed by microscopy to visualize Bcl10 in the cell.

33. The method of claim 28, wherein the step of detecting is performed by fluorescent microscopy to visualize Bcl10 in the cell.

34. The method of claim 28, wherein the step of detecting comprises detecting Bcl10 using an antibody that selectively binds to Bcl10.

35. The method of claim 28, wherein the method is performed as a high-throughput assay for screening multiple putative regulatory compounds simultaneously.

36. The method of claim 28, wherein the step of detecting comprises detecting a recombinant Bcl10 protein expressed by the cell.

37. The method of claim 28, wherein the step of detecting comprises detecting a Bcl10-reporter fusion protein expressed by the cell.

38. The method of claim 28, wherein the step of detecting comprises using biochemical extraction of Bcl10 from cells and detection of Bcl10 aggregates by biochemical fractionation techniques.

39. The method of claim 28, wherein the step of detecting Bcl10 aggregates comprises measuring changes in a refractive index of intact cells in which Bcl10 recombinantly expressed as compared to intact cell in which Bcl10 is not recombinantly expressed, or of Bcl10 separated from biochemical extracts of cells.

40. The method of claim 28, wherein the step of detecting Bcl10 aggregates comprises measuring changes in the light scatter properties of cells in which Bcl10 is recombinantly expressed as compared to intact cells in which Bcl10 is not recombinantly expressed.

41. The method of claim 28, wherein the step of contacting the cell with a putative regulatory compound is performed before the step of contacting the cell with the stimulus.

42. The method of claim 28, wherein the step of detecting comprising detecting whether the putative regulatory compound increases or decreases the translocation of the aggregates of Bcl10 to a site of contact between the cell and the putative stimulus, wherein an increase in translocation indicates an increase in Bcl10 signal transduction and wherein a decrease in translocation indicates a decrease in Bcl10 signal transduction.

43. The method of claim 28, further comprising detecting a change in a characteristic of Bcl10 activity selected from the group consisting of a change in the level of Bcl10 expression and a change in the level of phosphorylation of Bcl10 in the cell, wherein a change in the level of Bcl10 expression or a change in the level of Bcl10 phosphorylation in the presence of the putative regulatory compound indicates that the putative regulatory compound regulates Bcl10 signal transduction.

44. The method of claim 28, wherein the cell is a T lymphocyte.

45. The method of claim 44, wherein the method comprises:
a) contacting a T lymphocyte having a T cell antigen receptor (TCR) with a stimulus that activates the T lymphocyte through the TCR signal transduction pathway;
b) contacting the T lymphocyte with a putative regulatory compound under conditions in which, in the absence of the putative regulatory compound, Bcl10 polymerizes by forming aggregates in the T lymphocyte; and
c) detecting whether the level of the aggregates of Bcl10 in the T lymphocyte increases or decreases in the presence of the putative regulatory compound as compared to in the absence of the putative regulatory compound, wherein an increase or decrease in the level of the aggregates of Bcl10 in the presence of the putative regulatory compound indicates that the compound regulates the Bcl10-mediated signal transduction in the cell.

46. The method of claim 28, wherein the cell is a B lymphocyte.

47. The method of claim 46, wherein the method comprises:
- a) contacting a B lymphocyte having a B cell antigen receptor (BCR) with a stimulus that activates the B lymphocyte through the BCR signal transduction pathway;
- b) contacting the B lymphocyte with a putative regulatory compound under conditions in which, in the absence of the putative regulatory compound, Bcl10 polymerizes by forming aggregates in the B lymphocyte; and
- c) detecting whether the level of the aggregates of Bcl10 in the B lymphocyte increases or decreases in the presence of the putative regulatory compound as compared to in the absence of the putative regulatory compound, wherein an increase or decrease in the level of the aggregates of Bcl10 in the presence of the putative regulatory compound indicates that the compound regulates the Bcl10-mediated signal transduction in the cell.

* * * * *

UNITED STATES PATENT AND TRADEMARK OFFICE
CERTIFICATE OF CORRECTION

| | |
|---|---|
| PATENT NO. | : 7,169,570 B2 |
| APPLICATION NO. | : 10/795157 |
| DATED | : January 30, 2007 |
| INVENTOR(S) | : Schaefer et al. |

It is certified that error appears in the above-identified patent and that said Letters Patent is hereby corrected as shown below:

Claim 14:

Column 50, line 17, delete "culturing" and insert --contacting-- therein.

Claim 31

Column 51, line 57, delete "to the site" and insert --to a site-- therein.

Claim 39

Column 52, line 16, insert the word --is-- after the word "Bcl10".

Column 52, line 17, delete "cell" and insert --cells-- therein.

Claim 42

Column 52, line 30, delete "comprising" and insert --comprises-- therein.

Signed and Sealed this

Twenty-second Day of May, 2007

JON W. DUDAS
*Director of the United States Patent and Trademark Office*